(12) United States Patent
Simpson et al.

(10) Patent No.: US 10,702,397 B2
(45) Date of Patent: *Jul. 7, 2020

(54) INSERTION HANDLE FOR SURGICAL IMPLANTS

(71) Applicant: Howmedica Osteonics Corp., Mahwah, NJ (US)

(72) Inventors: Philip J. Simpson, Escondido, CA (US); George A. Mansfield, III, San Diego, CA (US); Damien J. Shulock, San Francisco, CA (US); David G. Matsuura, Del Mar, CA (US); Walter Dean Gillespie, San Diego, CA (US); John E. Ashley, Danville, CA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 114 days.

This patent is subject to a terminal disclaimer.

(21) Appl. No.: 15/996,642

(22) Filed: Jun. 4, 2018

(65) Prior Publication Data

US 2018/0344482 A1 Dec. 6, 2018

Related U.S. Application Data

(63) Continuation of application No. 14/645,843, filed on Mar. 12, 2015, now Pat. No. 9,987,149, which is a (Continued)

(51) Int. Cl.
*A61B 17/46* (2006.01)
*A61F 2/46* (2006.01)
*A61F 2/30* (2006.01)

(52) U.S. Cl.
CPC ... *A61F 2/4611* (2013.01); *A61F 2002/30133* (2013.01); *A61F 2002/30538* (2013.01); (Continued)

(58) Field of Classification Search
CPC .................. A61F 2/46; A61F 2/4611
See application file for complete search history.

(56) References Cited

U.S. PATENT DOCUMENTS 6,764,491 B2 7/2004 Frey et al.
6,830,570 B1 12/2004 Frey et al.
(Continued)

FOREIGN PATENT DOCUMENTS

WO 9531948 A1 11/1995
WO 2002017823 A1 3/2002
(Continued)

OTHER PUBLICATIONS

European Search Report for EP Application No. 18194369.7, dated Feb. 11, 2019.
(Continued)

*Primary Examiner* — Christopher J Beccia
(74) *Attorney, Agent, or Firm* — Lerner, David, Littenberg, Krumholz & Mentlik, LLP

(57) ABSTRACT

An insertion handle for medical implants includes a handle with an elongate shaft extending therefrom and connection means for the implant disposed at the end of the shaft opposite the handle. The connection means includes a pivotable attachment for the implant that is controlled remotely from the handle. Both angle of the implant with respect to the handle and shaft as well as the attachment may be separately controlled and adjusted. Remote angular adjustment facilitates insertion of implants in to small surgical sites because the orientation of the implant may be repeatedly, remotely adjusted as the implant is inserted. Connectors may also be provided at the engagement surface between the handle and implant in order to provide communication with the implant or surgical site. The connectors also may serve as torque bearing members to avoid the need (Continued)

for separate torque bearing means such as keyways and the like.

20 Claims, 31 Drawing Sheets

Related U.S. Application Data continuation of application No. 13/264,498, filed as application No. PCT/US2010/031247 on Apr. 15, 2010, now Pat. No. 8,998,924.

(60) Provisional application No. 61/212,808, filed on Apr. 16, 2009.

(52) U.S. Cl.
CPC ............ *A61F 2002/4628* (2013.01); *A61F 2230/0015* (2013.01); *A61F 2250/0006* (2013.01)

(56) References Cited

U.S. PATENT DOCUMENTS

| | | | |
|---|---|---|---|
| 6,830,574 B2 | 12/2004 | Heckele et al. | |
| 7,060,073 B2 | 6/2006 | Frey et al. | |
| 7,118,579 B2 | 10/2006 | Michelson | |
| 7,235,082 B2 | 6/2007 | Bartish et al. | |
| 7,500,991 B2 | 3/2009 | Bartish, Jr. et al. | |
| 7,575,580 B2 | 8/2009 | Lim et al. | |
| 7,708,779 B2 | 5/2010 | Edie et al. | |
| 7,811,292 B2 | 10/2010 | Lo et al. | |
| 7,892,239 B2* | 2/2011 | Warnick | A61F 2/4465 606/279 |
| 7,976,549 B2 | 7/2011 | Dye et al. | |
| 7,985,256 B2 | 7/2011 | Grotz et al. | |
| 7,988,695 B2* | 8/2011 | Dye | A61F 2/4611 606/86 A |
| 8,043,293 B2 | 10/2011 | Warnick | |
| 8,147,554 B2 | 4/2012 | Hansell et al. | |
| 8,157,845 B2 | 4/2012 | Warnick et al. | |
| 8,216,317 B2 | 7/2012 | Thibodeau | |
| 8,241,364 B2 | 8/2012 | Hansell et al. | |
| 8,252,060 B2 | 8/2012 | Hansell et al. | |
| 8,343,224 B2 | 1/2013 | Lynn et al. | |
| 8,414,590 B2 | 4/2013 | Oh et al. | |
| 8,419,795 B2 | 4/2013 | Sweeney | |
| 8,506,636 B2 | 8/2013 | Dye | |
| 8,992,620 B2 | 3/2015 | Ashley et al. | |
| 8,998,924 B2* | 4/2015 | Simpson | A61F 2/4611 606/105 |
| 9,808,354 B2* | 11/2017 | Willis | A61B 17/8858 |
| 9,987,149 B2* | 6/2018 | Simpson | A61F 2/4611 |
| 2001/0021853 A1 | 9/2001 | Heckele et al. | |
| 2002/0049449 A1 | 4/2002 | Bhatnagar et al. | |
| 2005/0113842 A1 | 5/2005 | Bertagnoli et al. | |
| 2005/0131419 A1* | 6/2005 | McCord | A61B 17/7085 606/99 |
| 2005/0209698 A1 | 9/2005 | Gordon et al. | |
| 2006/0235426 A1 | 10/2006 | Lim et al. | |
| 2007/0093897 A1* | 4/2007 | Gerbec | A61F 2/4465 623/17.11 |
| 2007/0142843 A1 | 6/2007 | Dye | |
| 2007/0179614 A1 | 8/2007 | Heinz et al. | |
| 2007/0225726 A1* | 9/2007 | Dye | A61F 2/4465 606/99 |
| 2008/0065082 A1 | 3/2008 | Chang et al. | |
| 2008/0077150 A1 | 3/2008 | Nguyen | |
| 2008/0091211 A1* | 4/2008 | Gately | A61B 17/1671 606/99 |
| 2008/0161933 A1 | 7/2008 | Grotz et al. | |
| 2008/0221694 A1 | 9/2008 | Warnick et al. | |
| 2008/0306557 A1 | 12/2008 | Altarac et al. | |
| 2009/0043312 A1 | 2/2009 | Koulisis et al. | |
| 2009/0177236 A1 | 7/2009 | Saab et al. | |
| 2009/0248163 A1 | 10/2009 | King et al. | |
| 2011/0230970 A1 | 9/2011 | Lynn et al. | |
| 2011/0276142 A1 | 11/2011 | Niemiec et al. | |
| 2012/0041557 A1 | 2/2012 | Frigg | |
| 2014/0303730 A1 | 10/2014 | McGuire et al. | |
| 2017/0290671 A1 | 10/2017 | Milz et al. | |
| 2017/0290680 A1 | 10/2017 | Pinal et al. | |

FOREIGN PATENT DOCUMENTS

| | | |
|---|---|---|
| WO | 2008041972 A2 | 4/2008 |
| WO | 2008131498 A1 | 11/2008 |

OTHER PUBLICATIONS

Extended European Search Report for Application No. 15189369.0 dated May 4, 2016.
International Search Report and Written Opinion dated Nov. 11, 2010 in relation International Application No. PCT/US2010/031247.
Supplementary European Search Report, dated Aug. 27, 2013, in connection with related EU10765185.3.

* cited by examiner

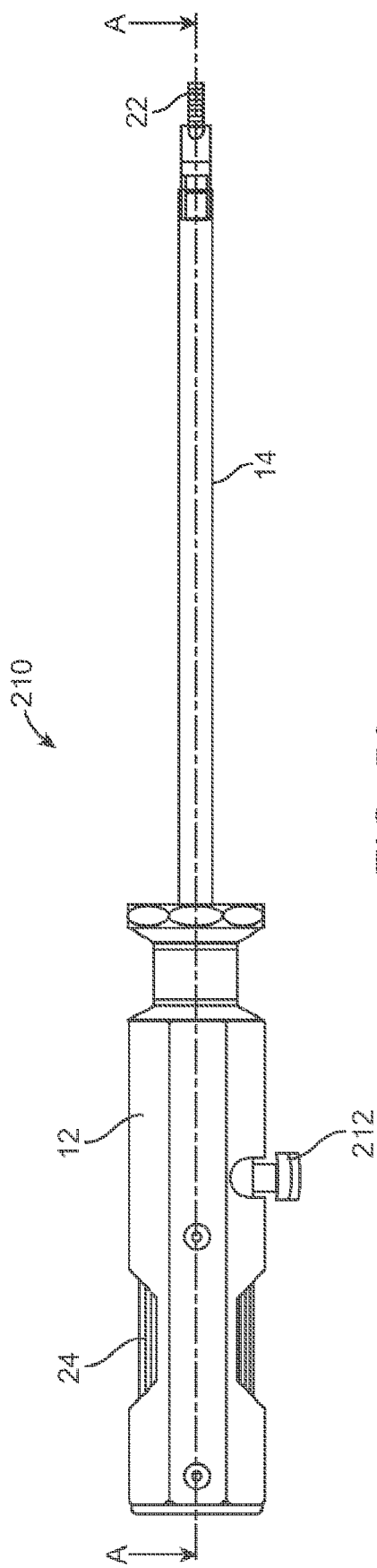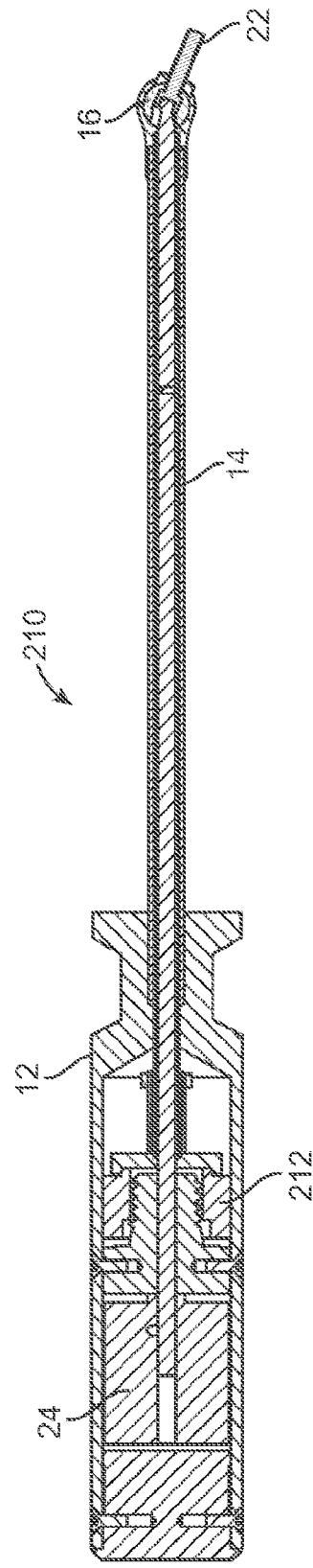
FIG. 5A
FIG. 5B

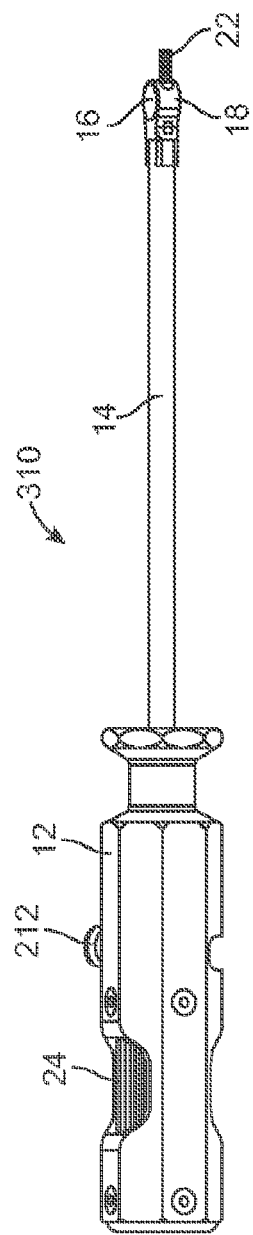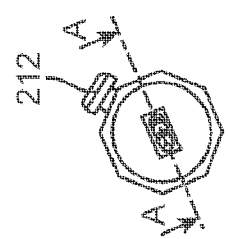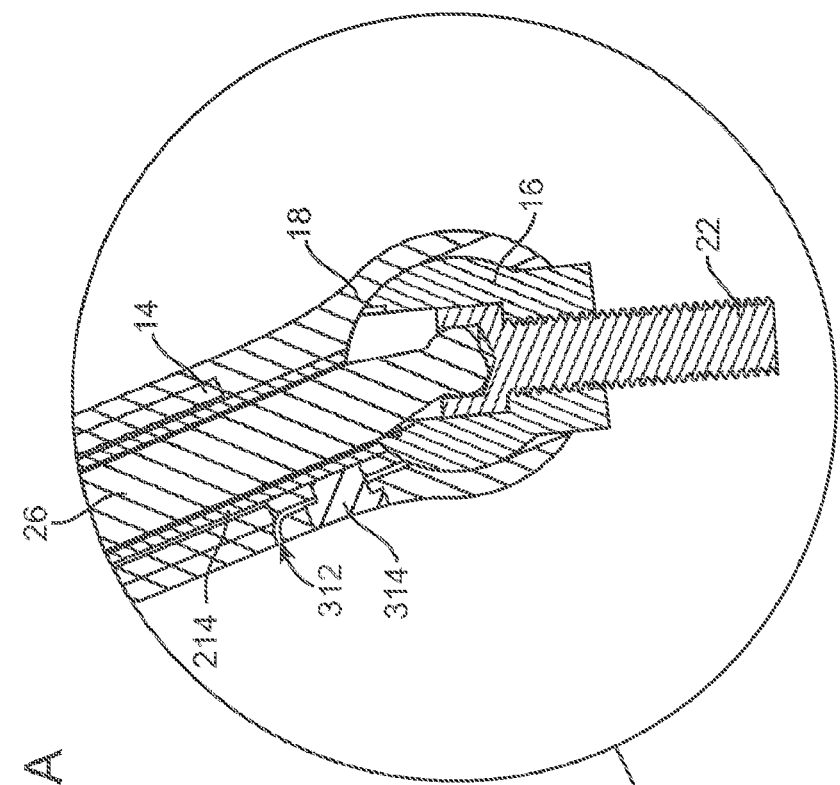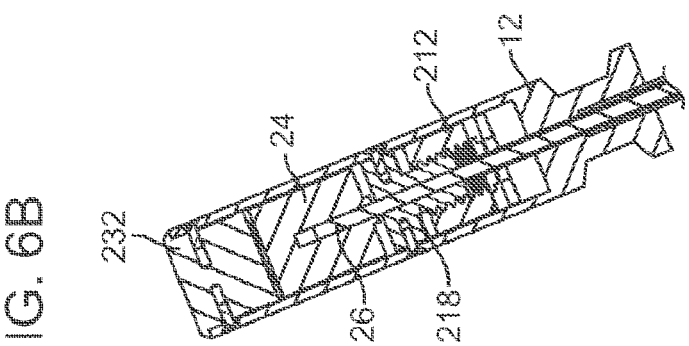
FIG. 6A
FIG. 6B
FIG. 6C
FIG. 6D

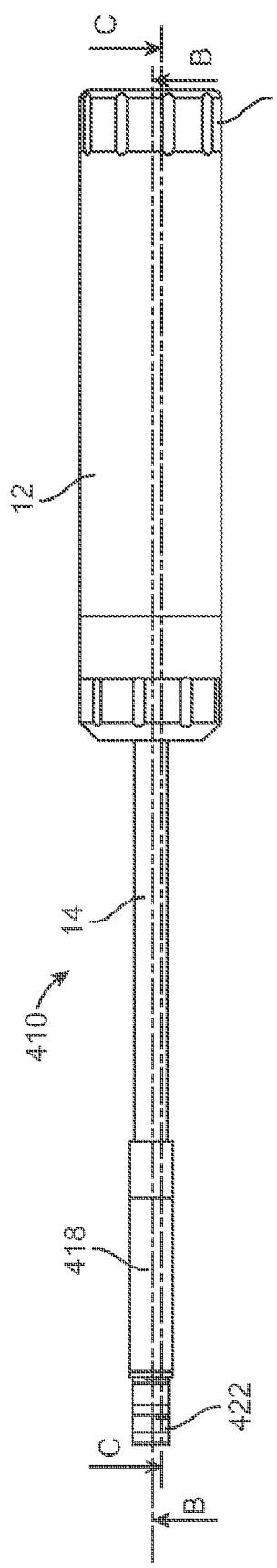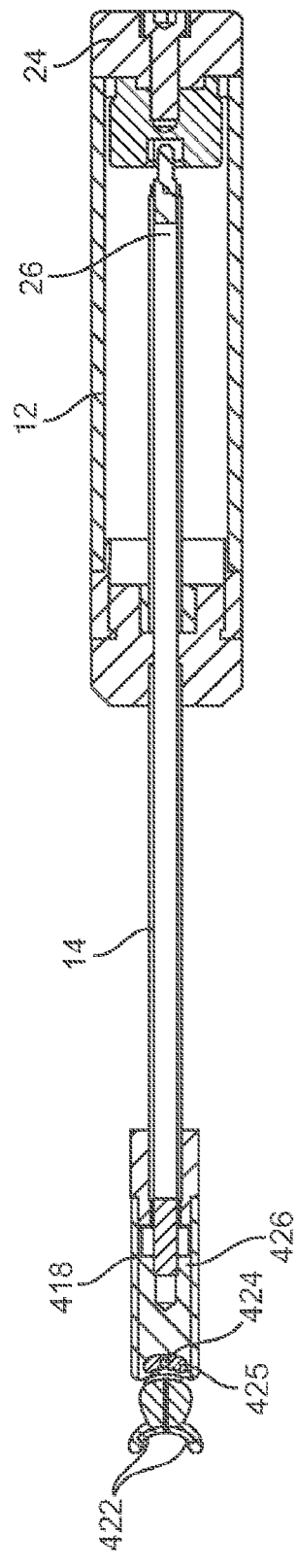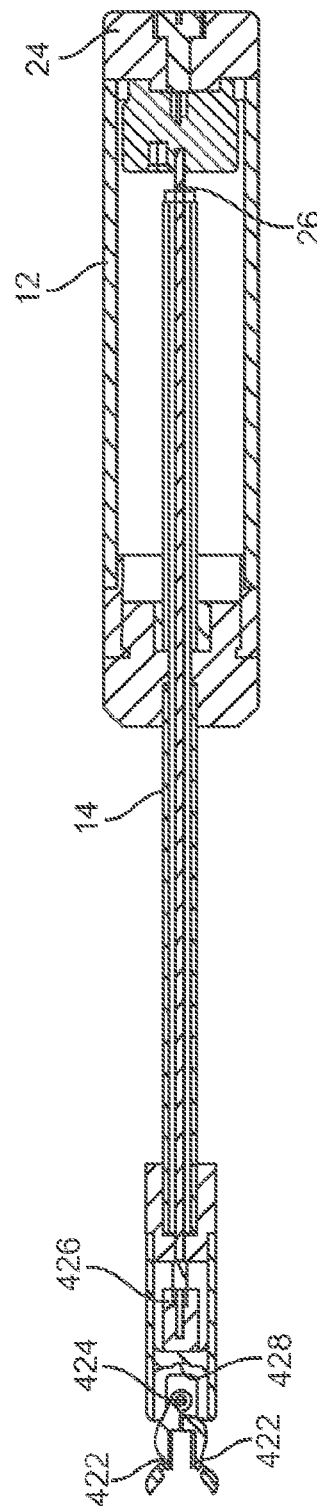
FIG. 7B
FIG. 7C
FIG. 7D

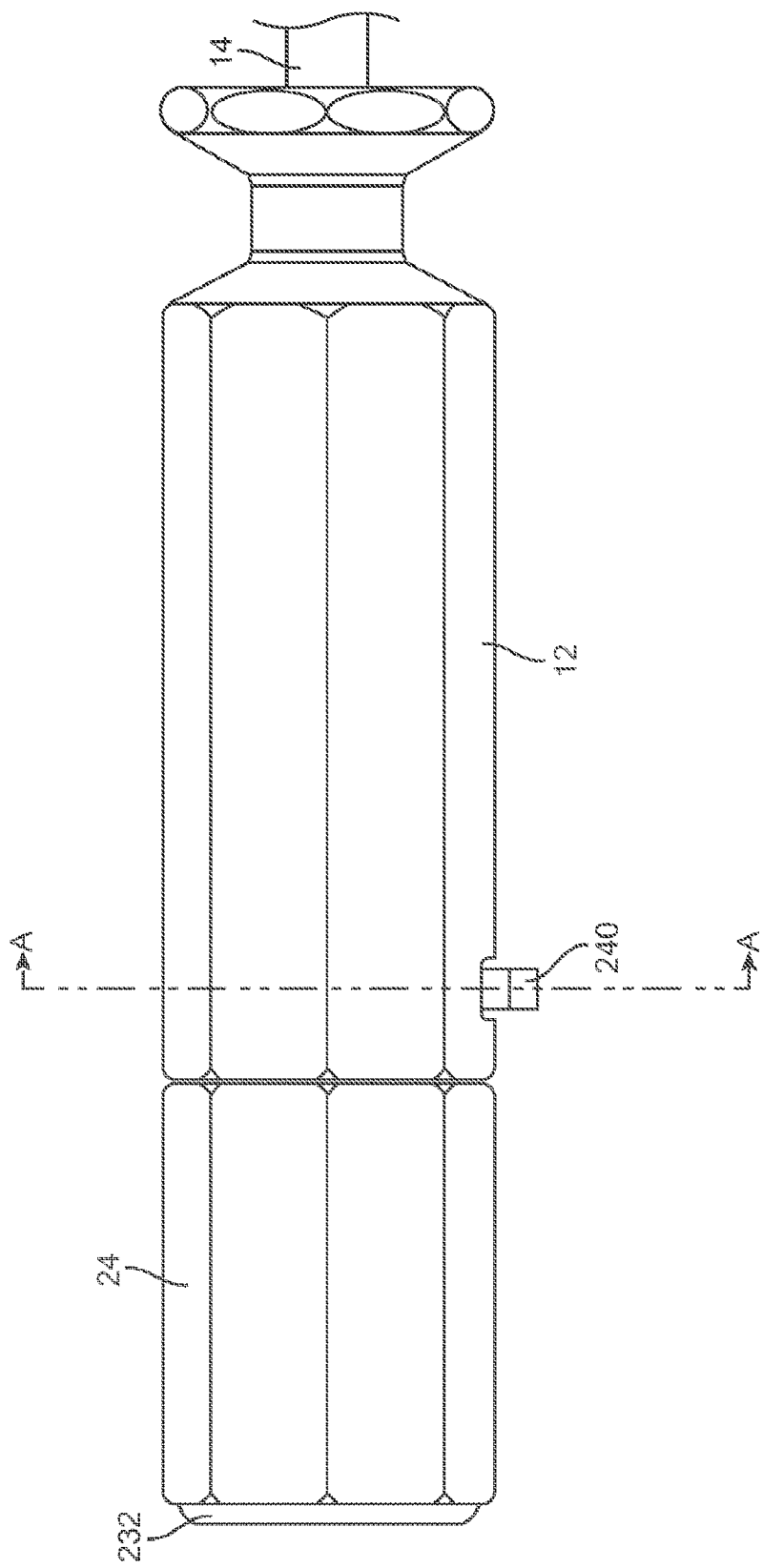

INSERTION HANDLE FOR SURGICAL IMPLANTS

CROSS-REFERENCE TO RELATED APPLICATIONS

The present application is a continuation of U.S. patent application Ser. No. 14/645,843, filed Mar. 12, 2015, which is a continuation of U.S. patent application Ser. No. 13/264,498, filed on Nov. 17, 2011, which is a national phase entry under 35 U.S.C. § 371 of International Application No. PCT/US2010/31247 filed on Apr. 15, 2010, which claims priority from Provisional Application No. 61/212,808, filed on Apr. 16, 2009, the disclosures of which are incorporated herein by reference.

FIELD OF THE INVENTION

The present invention generally relates to the field of surgical tools such as tools used in orthopedic surgical procedures. In particular, embodiments of the present invention are directed to an insertion handle for implants such as spinal implants.

BACKGROUND

A variety of devices for holding, manipulating and inserting medical implants during surgical procedures are known in the art. As techniques for less-invasive surgeries are refined, surgical access openings are made increasingly smaller in an attempt to reduce patient trauma and recovery time.

In light of the developments in less-invasive surgeries, there is a continuing need for such devices that provide for greater and more precise control over the manipulation and orientation of implants being inserted.

SUMMARY OF THE DISCLOSURE

In one implementation, the present disclosure is directed to an apparatus for inserting a medical implant. The apparatus includes: a handle; an outer shaft extending from the handle along a shaft axis; an inner control shaft extending through the outer shaft along the shaft axis; an actuator disposed with the handle and cooperating with the inner control shaft to move the inner control shaft within the outer shaft in response to user manipulation of the actuator; and pivotable connection means disposed on the outer shaft opposite the handle and cooperating with the inner shaft to engage or release an implant, and to angularly position the implant with respect to the shaft axis in response to movement of the inner control shaft, the pivotable connection means including user selectable lock means for selectively locking an implant engaged thereon at a fixed angle relative to the shaft axis.

In another implementation, the present disclosure is directed to an apparatus for inserting a medical implant. The apparatus includes: a handle; an outer shaft extending from the handle along a shaft axis; a rotatable inner shaft extending through the outer shaft along the shaft axis; an actuation member disposed with the handle and cooperating with the inner shaft to permit user rotation of the inner shaft; a distal end member mounted on the outer shaft opposite the handle, the distal end member having an annular wall defining an opening in a direction transverse to shaft axis with an inner engagement surface, and defining a window opening through the annular wall substantially in line with the outer shaft; a pivot member disposed within the opening defined by the annular wall of the distal end member, the pivot member having an outer engagement surface facing at least a portion of the inner engagement surface and being rotatable within the opening about an axis transverse to the shaft axis; and an attachment screw rotatably mounted in the pivot member and extending through the window opening along a screw axis, the attachment screw operatively connected to the inner shaft to permit rotational drive of the attachment screw through variable angles between the screw axis and shaft axis; wherein the annular wall is deformable at least in part in response to a medical implant being tightly threaded onto the attachment screw to force engagement between the engagement surfaces to selectively lock the pivot member at a fixed angle with respect to the shaft axis.

In still another implementation, the present disclosure is directed to a method for inserting a medical implant using an insertion handle. The method includes: attaching the medical implant to a distal end of the insertion handle wherein a first angle is formed between an axis of the implant and an axis of the insertion handle; locking the implant against rotation at the first angle; inserting the implant at a surgical site to a first position; unlocking the implant to permit rotation; changing the angle between the implant axis and the handle axis to a second angle; locking the implant against rotation at the second angle; inserting the implant to a final position; and detaching the insertion handle from the implant.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIG. 5A is a side view of yet another alternative embodiment of the present invention.

FIG. 5B is a cross-sectional view of the embodiment shown in FIG. 5A taken through Line A-A.

FIG. 6A is a side view of yet another alternative embodiment of the present invention.

FIG. 6B is a front end view of the embodiment shown in FIG. 6A.

FIG. 6C is a broken cross-sectional view of the embodiment shown in FIG. 6B taken through line A-A.

FIG. 6D is a detailed cross-sectional view of the pivoting head shown in FIG. 6C.

FIG. 7B is a side view of the embodiment shown in FIG. 7A.

FIG. 7C is a cross-sectional view of the embodiment shown in FIG. 7B taken through Line B-B.

FIG. 7D is a cross-sectional view of the embodiment shown in FIG. 7B taken through Line C-C.

FIG. 9A is a side view of the proximal end of yet another embodiment of the present invention.

DETAILED DESCRIPTION

Embodiments of the present invention pertain to a surgical device which is used to surgically place an implant into the desired location of the body. More particularly, embodiments of the present invention are designed to allow placement of an implant into a position that is rotationally different than the position in which it is first inserted into the body. Such rotationally variable placement is achieved in embodiments of the present invention while maintaining constant attachment to the implant to permit forcible manipulation thereof.

Figure 1:
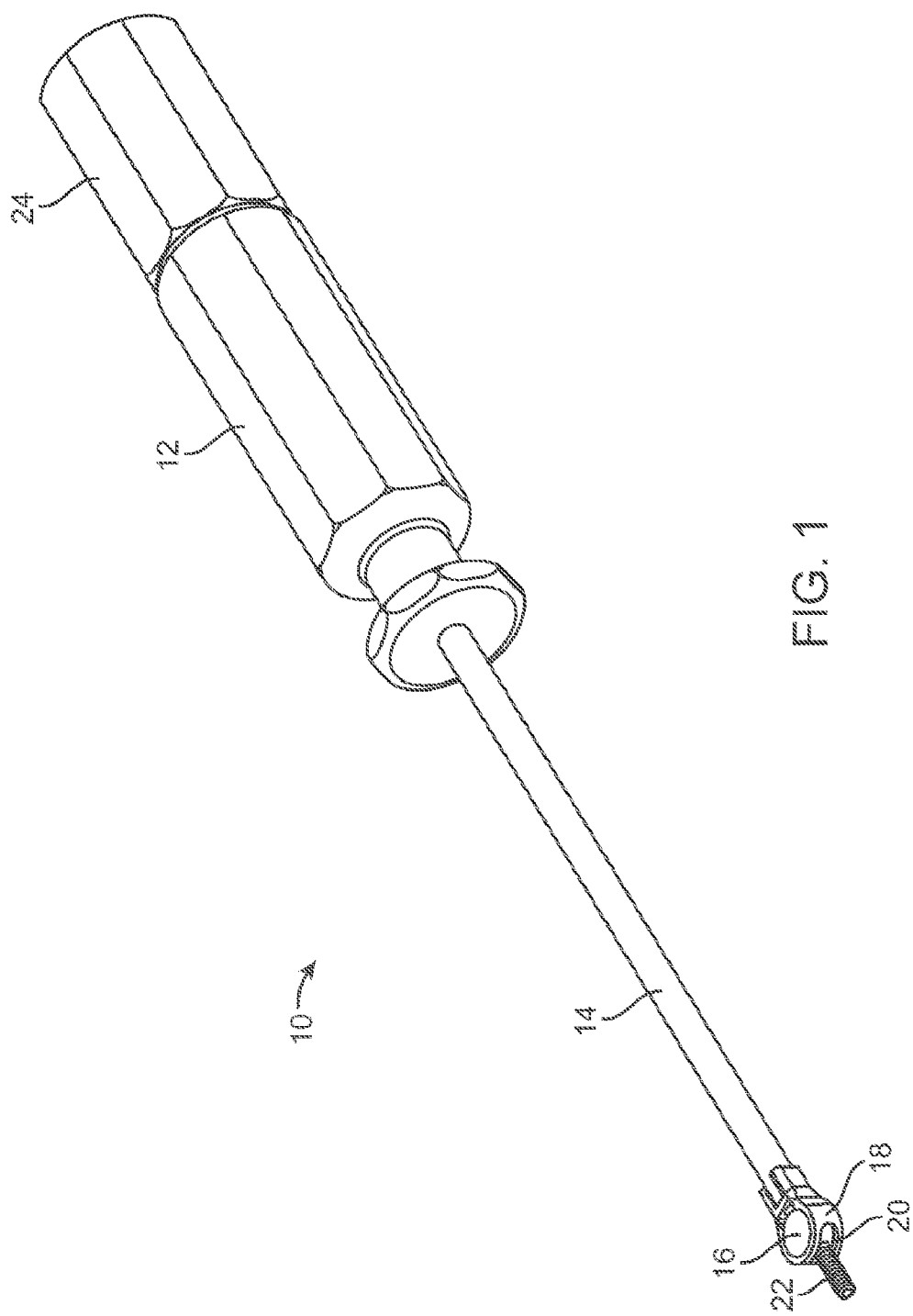
FIG. 1 is a perspective view of one embodiment of the present invention.

Turning now to FIG. 1, one embodiment of inserter 10 is shown, which is comprised of a handle 12, a shaft 14 attached thereto, a distal end member, formed for example, as a pivot cage 18 attached to the other end of the shaft 14, a pivot member or head 16 captured inside a transverse opening defined by the annular wall of the pivot cage 18 and an attachment screw 22 partially contained in the pivot head 16. The attachment screw 22 protrudes from the distal end of the inserter 10 from the pivot head 16 through the pivot cage 18 via the pivot cage window 20. At the proximal end of the handle is an attachment actuator 24 which is rotationally coupled to the attachment screw 22 as will be shown herein.

Figure 2A:
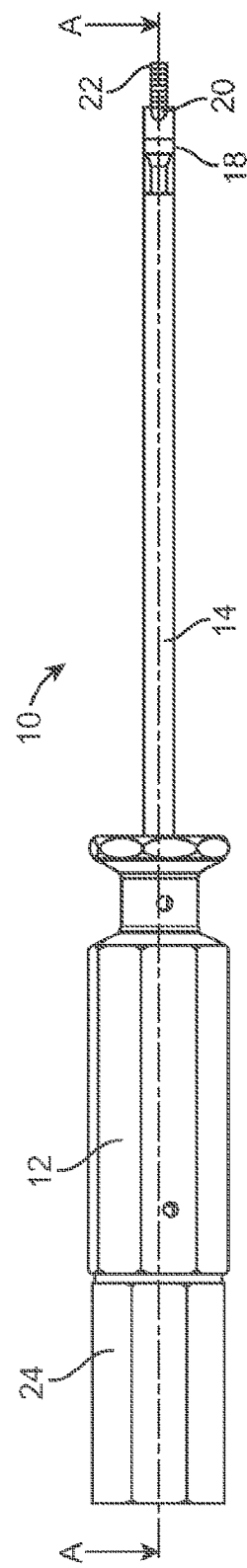
FIG. 2A is a side view of the embodiment shown in FIG. 1.
Figure 2B:
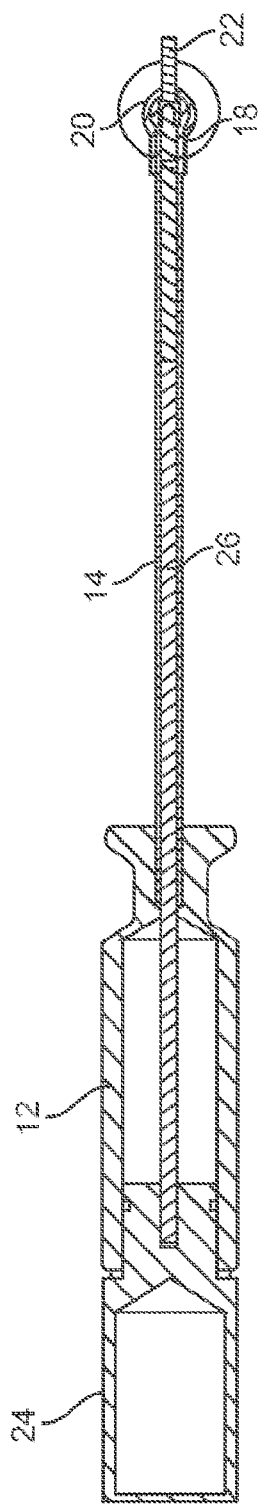
FIG. 2B is a cross-sectional view of the embodiment shown in FIG. 1 taken through Line A-A.
Figure 2C:
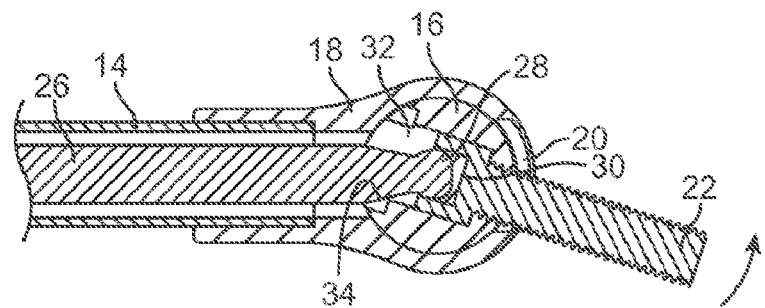
FIGS. 2C-2E are detailed cross-sectional views of the pivoting head shown in FIG. 2B in various angular positions.
Figure 2D:
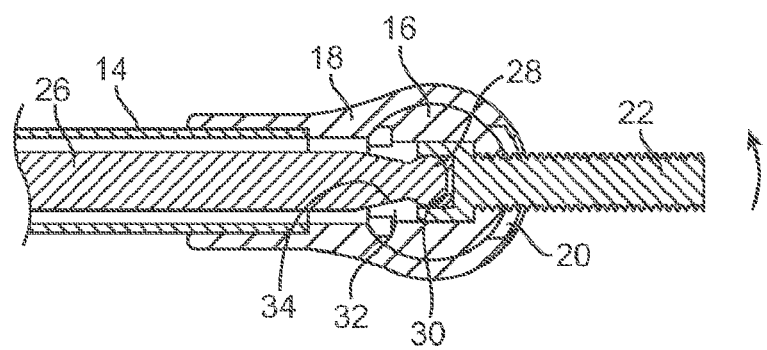
Figure 2E:
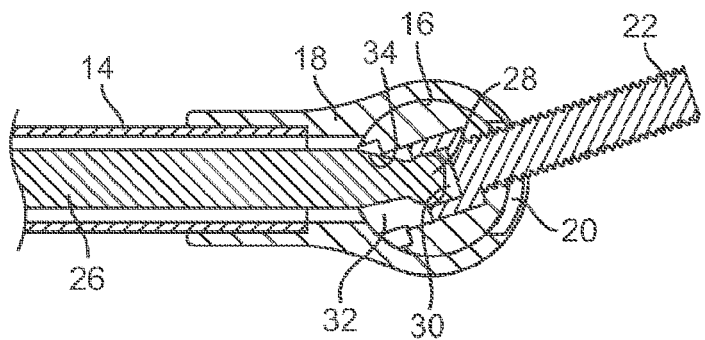

As can be seen in FIGS. 2A-2E, the attachment actuator 24 is connected to an attachment shaft 26 which passes through the inside of the handle 12 and the shaft 14. The attachment shaft distal end 28 has a hexagonal sided ball end shaped to engage the attachment screw interface 30. Interface 30 may be a socket configured to receive ball shaped distal end 28, thus forming a universal joint. This engagement of the attachment shaft distal end 28 and the attachment screw interface 30 enables rotational force applied by the user to the attachment actuator 24 to be transferred through the attachment shaft 26 to the attachment screw 22. This rotational force turns the screw to engage a medical implant. In this embodiment, the engagement and tightening of the medical implant (as will be explained in more detail herein) both attaches the implant to the inserter 10 and also rotationally locks the pivot head 16 to the pivot cage 18 fixing the angle between the insertion handle 12 and the implant. This rotation is accomplished by providing clearance for the attachment shaft 26 both by an attachment shaft taper 34 and with a pivot head pocket 32. The geometry of the pivot head pocket 32, the attachment shaft taper 34 and the pivot cage window 20 allows the pivot head 16 and attachment screw 22 to rotate through a predetermined angle as shown in FIGS. 2C-2E. This angle can be designed as needed to allow for the appropriate amount of rotation of the implant relative to the inserter 10 as will be described in more detail below.

Figure 3A:
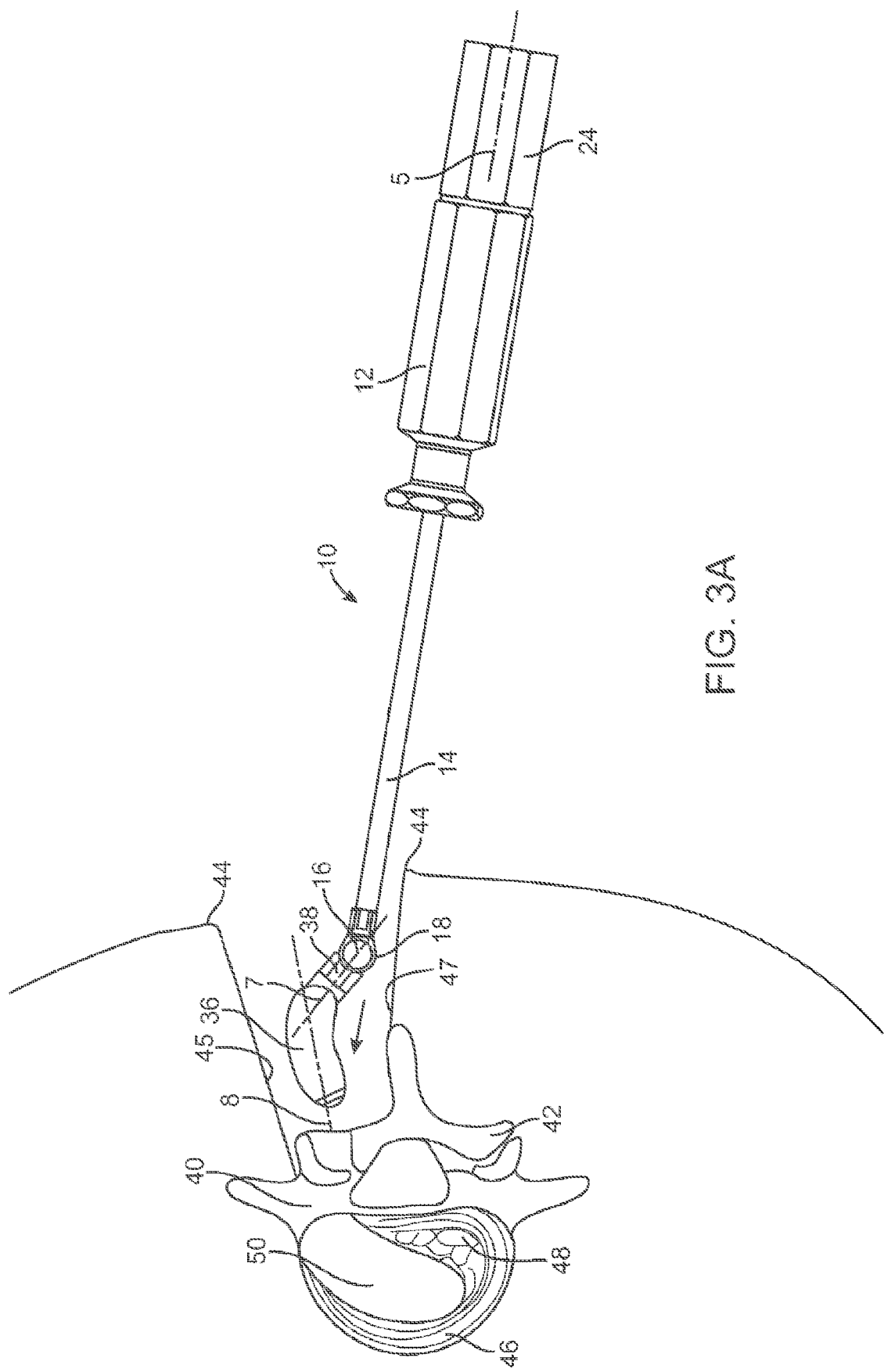
FIGS. 3A-3E illustrate an implantation sequence of top views of an embodiment of the present invention with an implant and a surgical treatment site shown.

FIGS. 3A-3E depict the inserter 10 being used to place an implant 36 into an intervertebral space 50 in a patient's spine, and the use of one embodiment of a user selectable lock means to position the implant angularly with respect to the inserter longitudinal axis to facilitate placement. In FIG. 3A, implant 36 is attached to the inserter 10 via an implant interface 38 which conforms to the pivot cage 18. Implant 36 has an elongated shape along implant axis 8. Implant axis 8 is oriented at a predetermined angle to screw axis 7 along attachment screw 22. Due to the pivotability of pivot head 16, the angle between the implant axis 8 and the longitudinal axis 5 of shaft 14 may be selected by the user as described herein.

Rotation of the attachment actuator 24 threads the attachment screw 22 through the implant interface 38 into the implant 36. The implant 36 is also fixed at a predetermined angle relative to the inserter 10 by rotation of the attachment screw 22 into the implant until the implant 36 is pressed against the implant interface 38 which in turn is pressed against the pivot cage 18 which in turn is compressed against the pivot head 16. Thus, in this embodiment the user selectable lock means comprises the annular walls of the pivot cage 18 being deformable at least in part so that the inner surface of the annular wall can engage at least part of the outer surface of pivot head 16. In this manner, the compressed assembly clamps the pivot head 16 and pivot cage 18 together and prevents rotation of the pivot head 16. It will be apparent to those schooled in the art that the implant interface 38 is not required to accomplish the attachment of the inserter 10 to the implant 36, neither is it required to accomplish the prevention of rotation of the pivot head 16. Alternate embodiments of the current invention are possible which integrate the implant interface 38 as part of the pivot cage 18 or as part of the implant 36. The implant interface 38 is useful in that different implant interface 38 designs will enable the same inserter 10 to be used on many different implants 36.

Figure 3B:
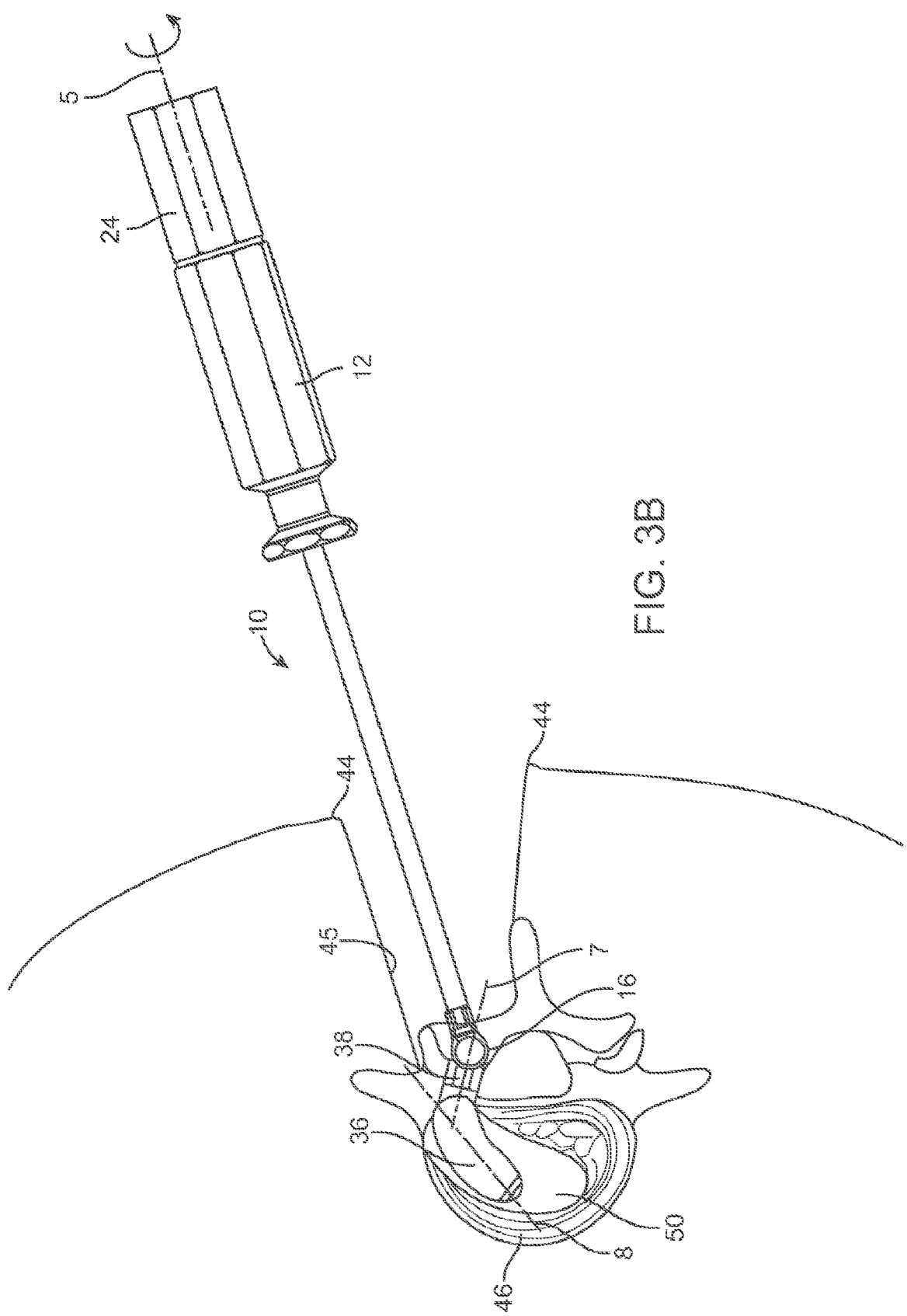
Figure 3C:
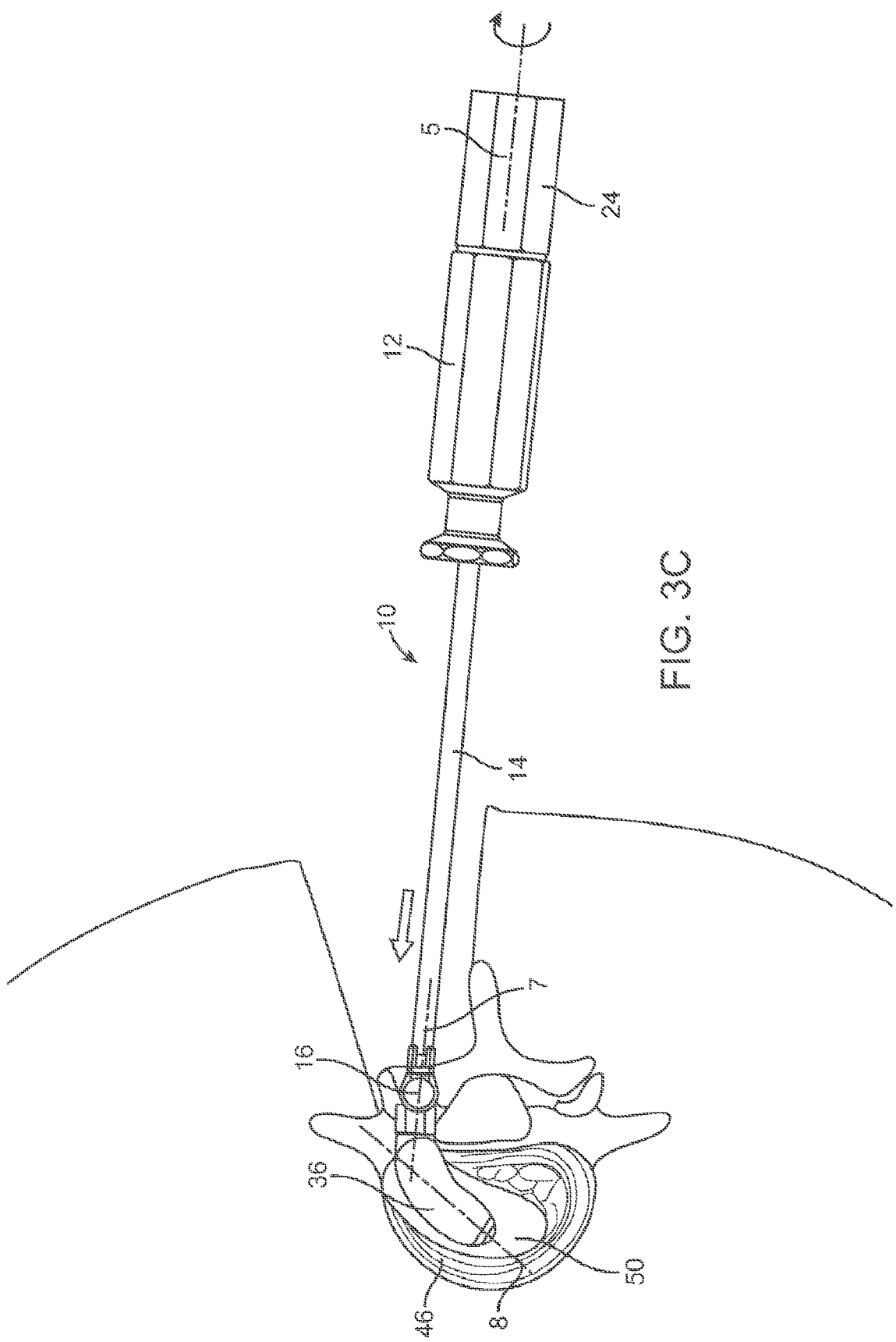

Returning to FIGS. 3A and 3B, the inserter 10 is used to guide the implant 36 accurately and safely through a narrow surgical opening 44 with a lateral side 45 and a medial side 47 created between an inferior vertebra 40 by removing the superior facet and a superior vertebra 42 by removing the inferior facet. The intervertebral space 50 is created by removing a portion of the disc annulus 46 and disc nucleus 48. As illustrated in FIG. 3A, the implant 36 is initially inserted along a straight insertion path (arrow) parallel to the medial side 47 and on the longitudinal axis 5 of the handle into the disc and then further up against the inner wall of the annulus 46 as shown in FIG. 3B. At this stage the implant axis 8 and the shaft axis 5 are at a first angle with respect to each other. This is not an optimal position for the implant 36. Rather there is a need to rotate the implant 36 to move it towards the center of the intervertebral space 50. This rotation may be accomplished in steps in this embodiment by first pivoting the inserter 10 towards the lateral side 45 of the surgical opening 44 and next by rotating the attachment actuator 24 (curved arrow) to rotate the attachment screw 22 and loosen the compression between the implant 36 and the pivot head 16. This release of compression allows the implant 36, attachment screw 22, and pivot head 16 to rotate when additional forward movement (hollow arrow) presses the implant 36 against the annulus 46 as shown in FIG. 3C. At the same time the insertion handle shaft 14 pivots back towards the medial side 47 of the surgical opening 44 to form a second angle between the implant axis 8 and the shaft axis 5. The attachment actuator 24 can then be rotated (curved arrow) back to compress the implant 36 against the implant interface 38 and lock the pivot head 16 in the pivot cage 18 to allow the inserter 10 to axially and pivotally advance the rotational locked implant 36.

Figure 3D:
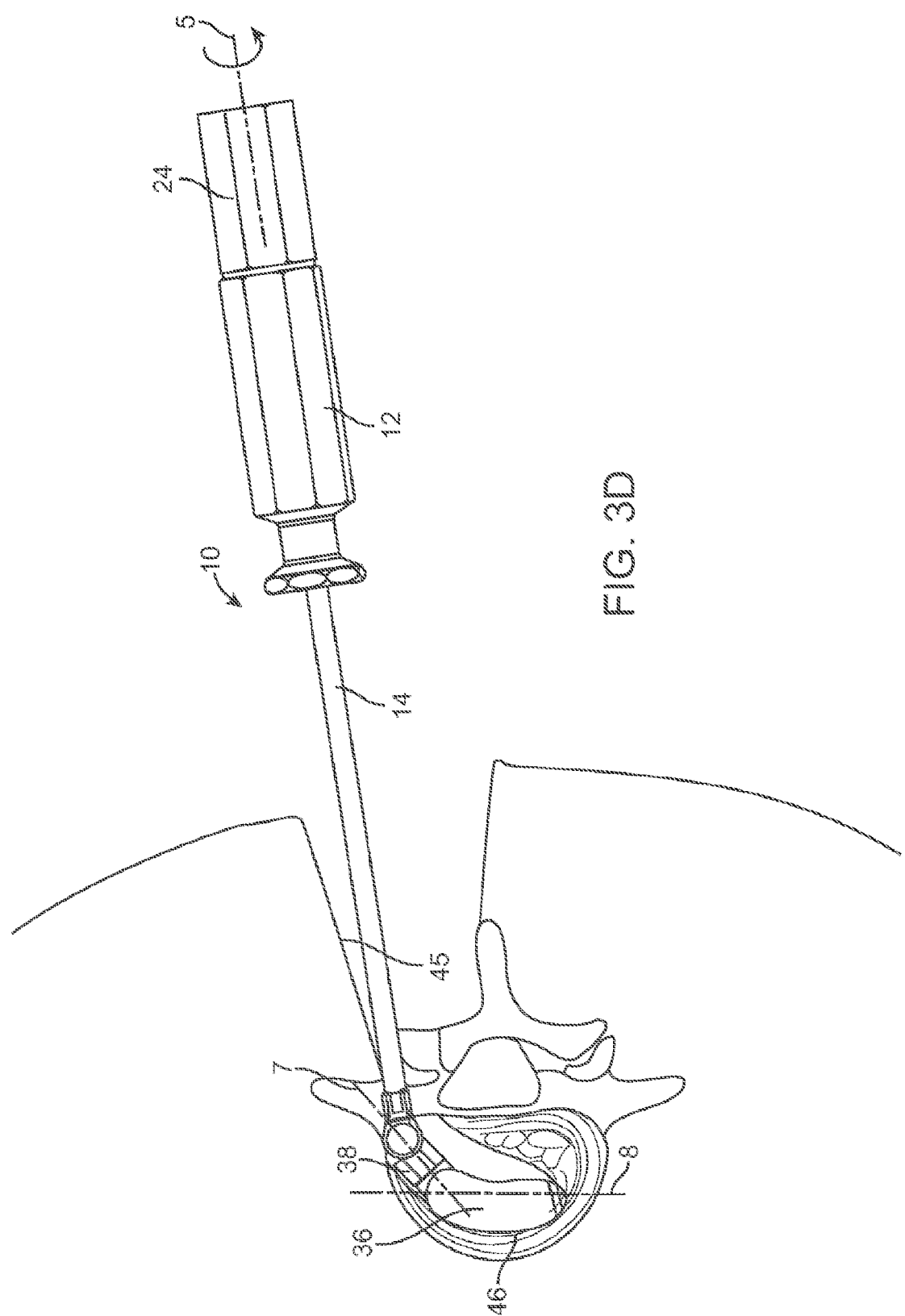

The process of locking the rotation, advancing and pivoting the inserter 10 and implant 36 as a unit, unlocking the attachment actuator 24 and pivoting the pivot cage 18 and implant 36, and relocking the rotation is repeated as necessary until the implant 36 is placed at the desired location as shown in FIG. 3D. Through this process the implant axis 8 is positioned at least at a third angle with respect to the shaft axis 5. Embodiments of the present invention thus allow placement of an implant 36, with a rotational orientation that is different from the original insertion orientation, into a surgical site through a much smaller surgical opening 44 with much smaller pivoting angle of the inserter 10 than otherwise possible.

Figure 3E:
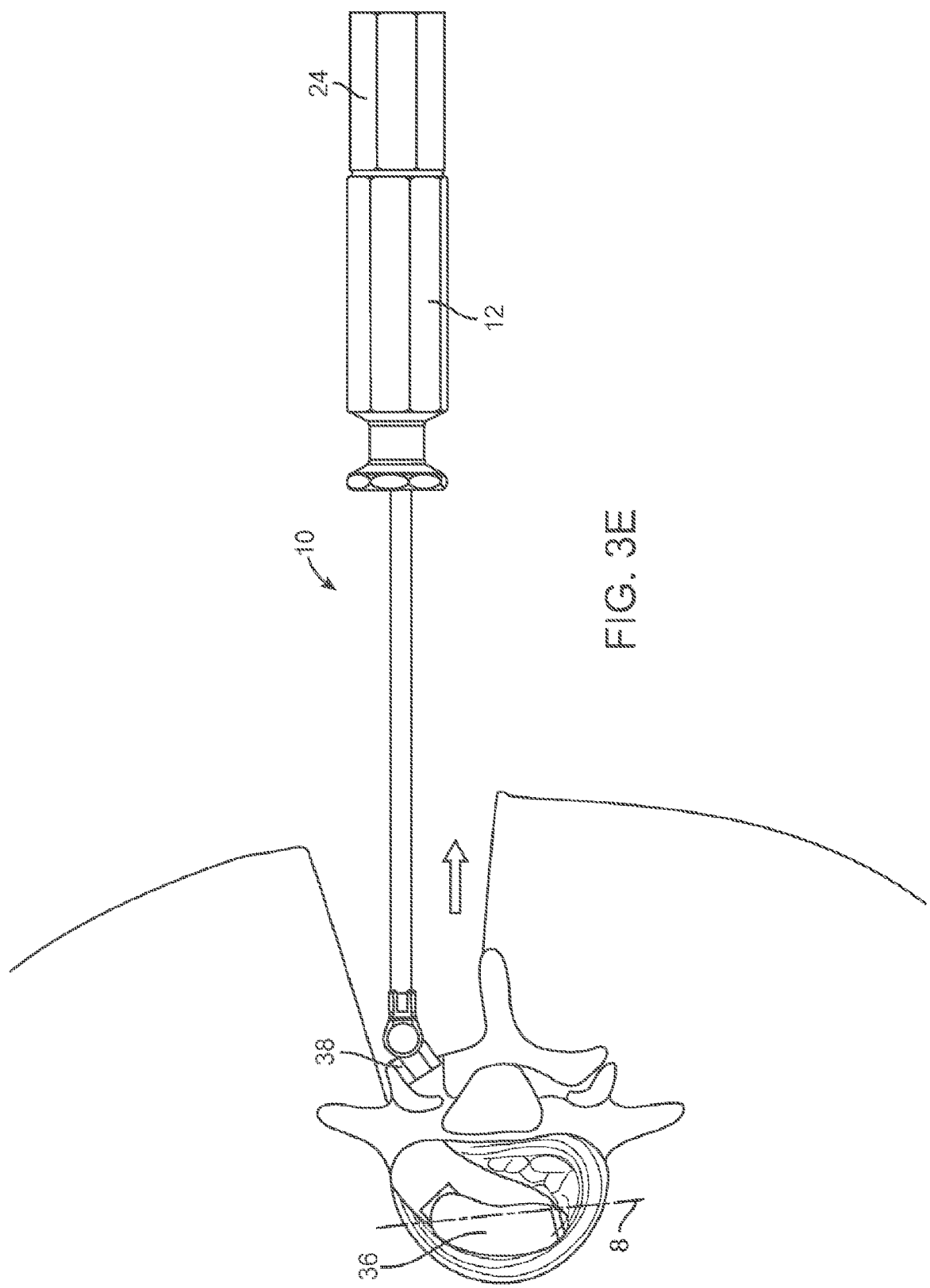

After placement of implant 36 at a desired location, the attachment actuator 24 is rotated (curved arrow) until the attachment screw 22 is completely removed from the implant. Then the inserter 10 and implant interface 38 can be removed (hollow arrow) from the surgical site leaving the implant 36 in place as shown in FIG. 3E. This illustrates just one of the many possible surgical sites were the inserter 10 can be used to advance and rotate a medical implant to a desired location in the body.

Figure 4:
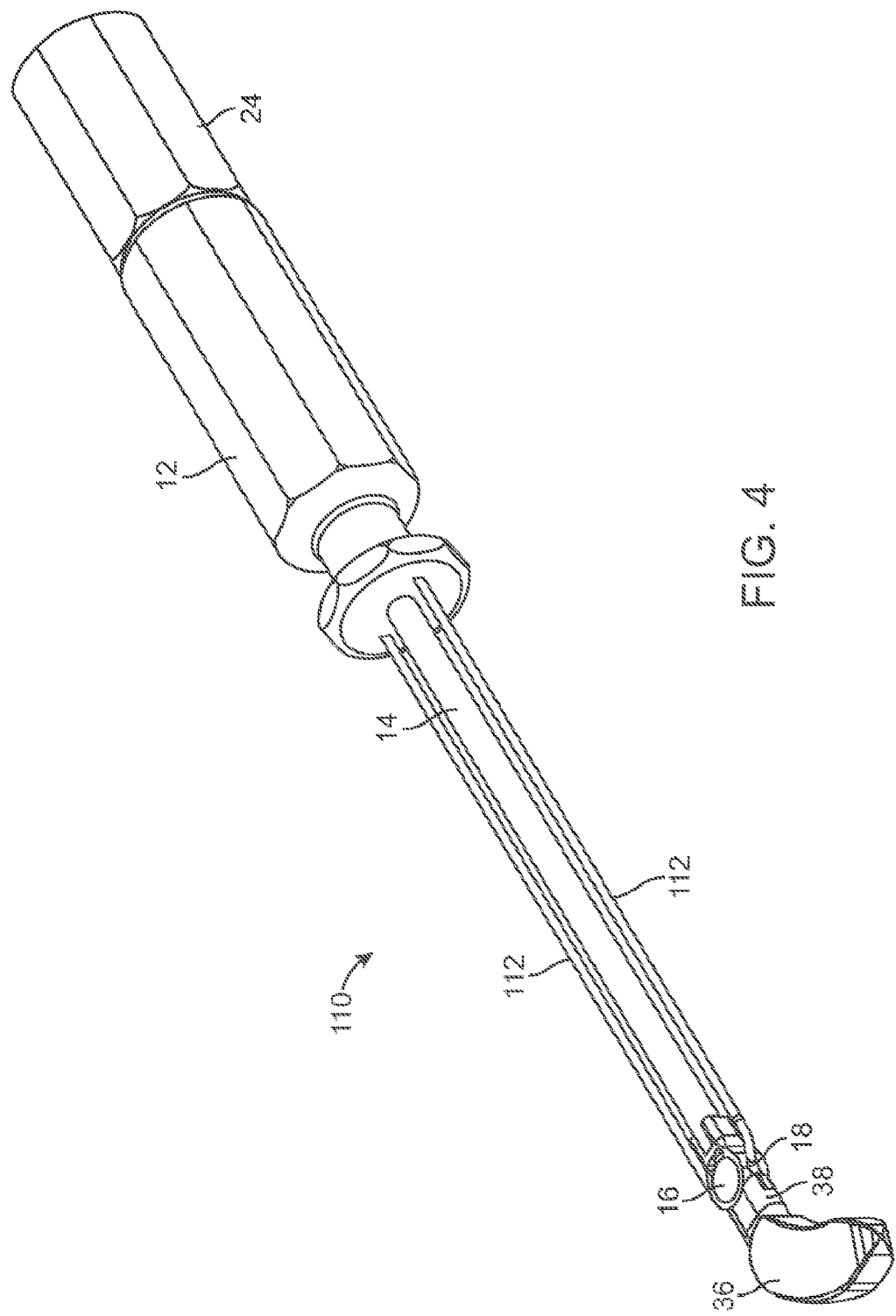
FIG. 4 is perspective view of an alternative embodiment of the present invention shown with an implant attached.
Figure 5C:
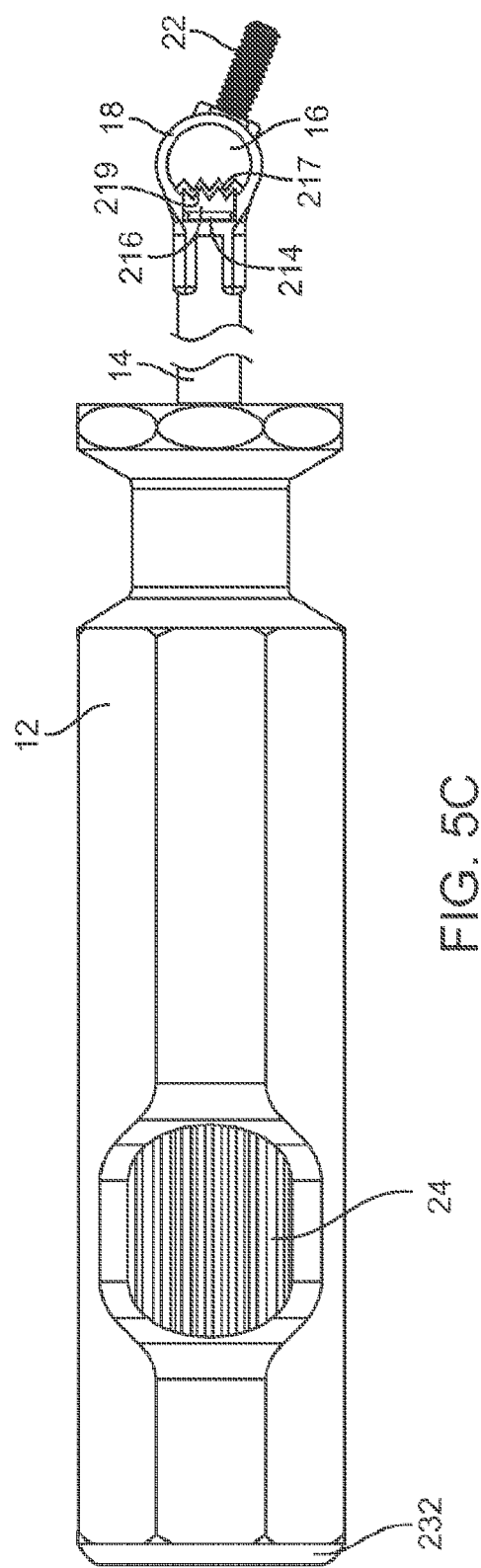
FIG. 5C is a broken top view of the embodiment shown in FIG. 5A.
Figure 5D:
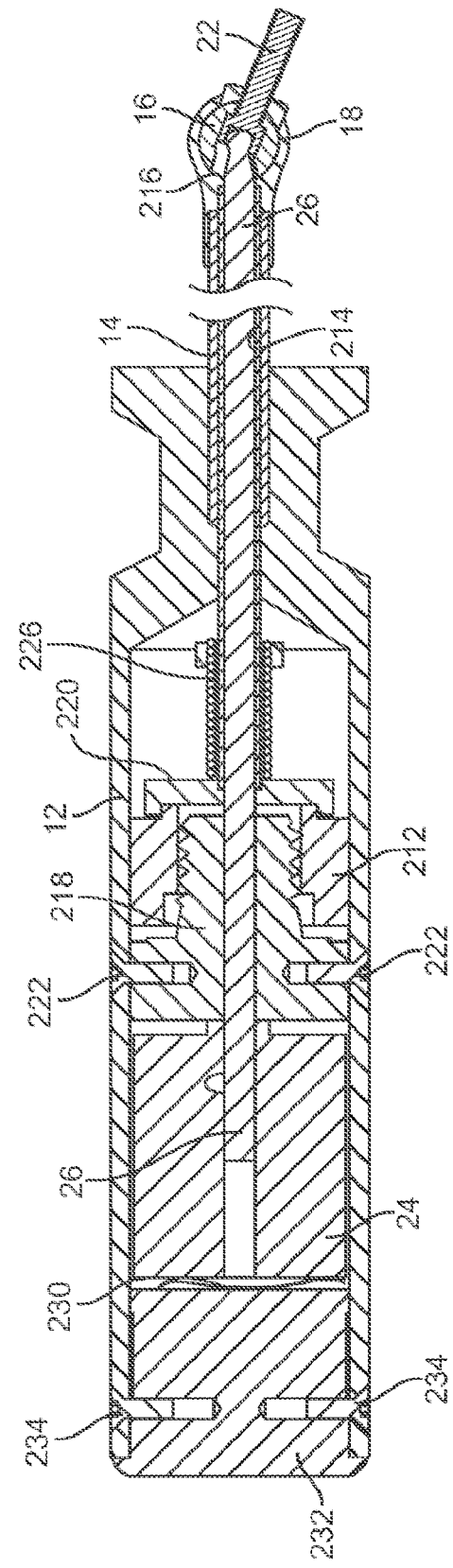
FIG. 5D is a broken cross-sectional view of the embodiment shown in FIG. 5A taken through line A-A.

Turning now to FIG. 4, an alternative embodiment of the present invention is shown. In this embodiment, inserter 110 includes access tubing 112, which are shown parallel to the shaft 14. Access tubing 112 connects the implant interface 38 to the handle 12. The access tubing 112 can be used for a number of functions such as delivering fluids or other materials through the handle 12 and implant interface 38 to the implant 36, removing materials from the implant 36, containing and/or guiding an actuator such as a tension line or rotator drive, or guiding light or electrical signals. Materials that can be delivered through the access tubing 112 include but are not limited to sterile saline, bone graft, bone morphogenic proteins, cement, medication, etc. It will be apparent to those skilled in the arts that the access tubing 112 can be directed inside the shaft 14 rather than external to it as shown in this figure.

FIGS. 5A-5D depict another embodiment of the present invention. In this embodiment, inserter 210 separates the implant 36 attachment function from the rotation function. There is both an attachment actuator 24 and a separate user selectable pivot lock actuator 212 in the handle 12. The attachment actuator 24 is connected to the attachment shaft 26, which when rotated rotates the attachment screw 22 to connect and disconnect to an implant (not shown). The pivot lock actuator 212 is attached to a pivot lock transfer plate 220, which in turn is attached to a pivot lock shaft 214. The pivot lock shaft 214 rides between the shaft 14 and the attachment shaft 26. When the pivot lock actuator 212 is rotated in one direction it advances forward on the threads of the pivot lock adjuster 218, which advances the pivot lock shaft 214 into the pivot lock 216, which is contained in the pivot cage 18. The pivot lock 216 has pivot lock engagement faces 217, which are configured to engage pivot head engagement faces 219 on the pivot head 16. When these faces engage, the pivot head 16 is locked rotationally with the pivot cage 18. When the pivot lock actuator 212 is rotated in the other direction it retracts backwards on the threads of the pivot lock adjuster 218. A pivot lock release actuator 226, which may be formed as a biasing element such as a coil spring, then retracts the pivot lock transfer plate 220 and the attached pivot lock shaft 214. This removes pressure on the pivot lock 216 and allows the pivot head 16 to rotate relative to the pivot cage 18. In this manner the inserter 210 allows the user to independently actuate the pivot locking and implant attachment functions. It will be apparent to those skilled in the art that this separation of functions can be useful to the surgeon who is using the inserter 210 to place an implant precisely in a patient's body.

The inserter 210 may also include pivot lock adjustment anchors 222 which lock the pivot lock adjuster 218 to the handle 12, and handle cap anchors 234, which attach a handle cap 232 to the handle 12. The handle cap 232 is useful in providing a surface for the surgeon to hammer against to force the implant 36 into a confined intervetebral space 50. The pivot lock adjuster 218 with its threads can be used to adjust the relative location of the advancement and retraction of the pivot lock actuator 212 and in turn the pivot lock transfer plate 220, pivot lock shaft 214, and pivot lock 216. This allows for adjustment of the locking movement and therefore the locking force between the pivot lock 216 and the pivot head 16. After this adjustment is made, the pivot lock adjuster anchors 222 fix the pivot lock adjuster 218 to the handle 12 and maintain this locking movement. It will be apparent to those skilled in the art that there are many other mechanisms possible to provide for the adjustment of the locking movement of the inserter 210 without departing from the present invention and this mechanism is provided as but one example.

There are also many ways to separate the attachment and rotation functions in embodiments of the present invention to provide separate user selectable lock means. Another such alternative embodiment is shown in the inserter 310 depicted in FIGS. 6A-6D. In this embodiment the pivot lock shaft 214 is connected to a pivot lock shaft pin 314, which is connected to the pivot cage 18. The pivot cage 18 has a pivot cage slot 312 proximal of the pivot lock shaft pin 314. In this embodiment the pivot lock shaft 214 is retracted via the pivot lock actuator 212 to pull on the pivot lock shaft pin 314, which reduces the pivot cage slot 312 and compresses the pivot cage 18 around the pivot head 16 locking it rotationally. This method of tensioning a portion of the pivot cage 18 to increase the force between the pivot cage 18 and the pivot head 16 and lock the pivot head 16 rotational is but one alternative. For example, in another alternative, the pivot cage 18 could also be tensioned radially to compress it around the pivot head 16 and lock the pivot head 16 rotationally to the pivot cage 18.

Figure 7A:
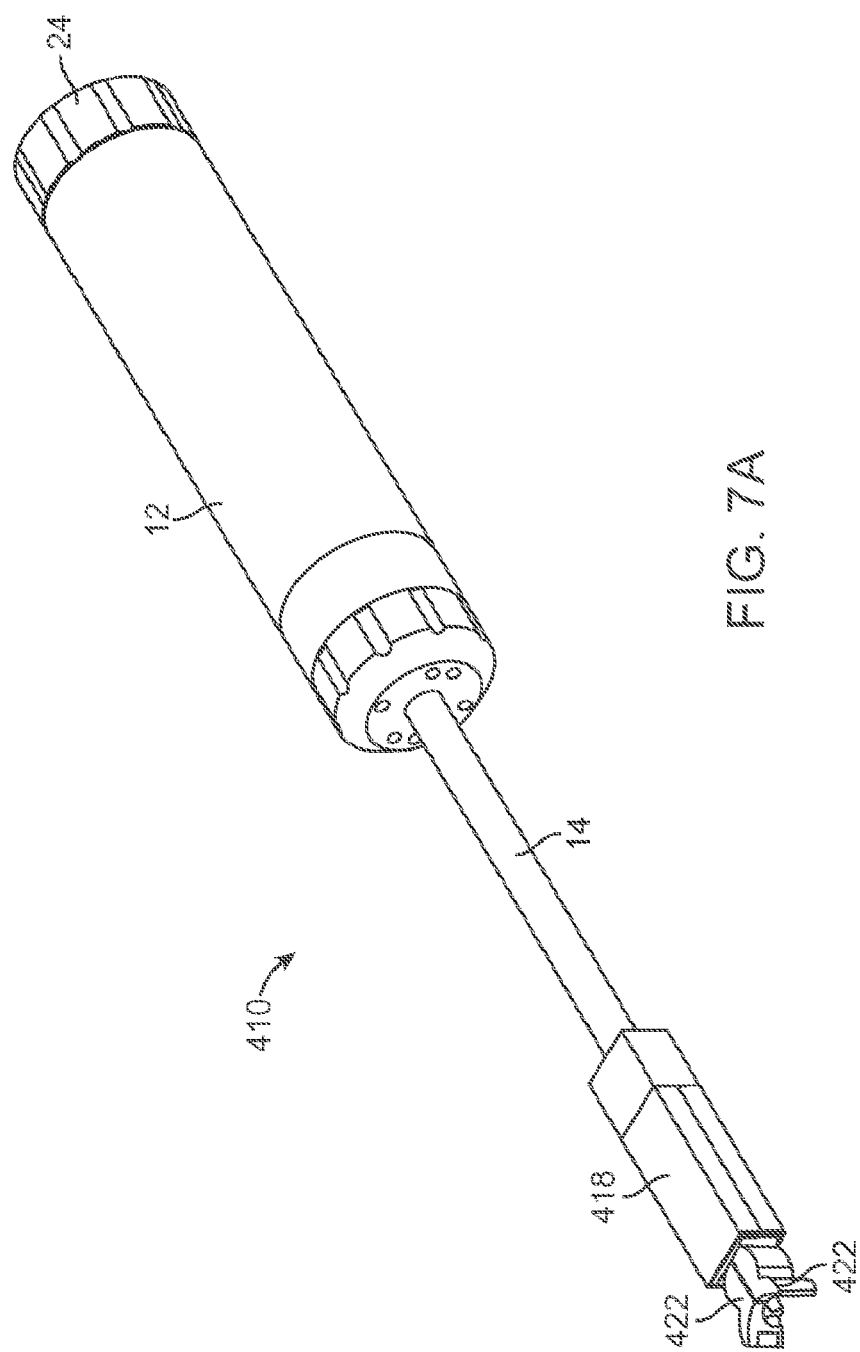
FIG. 7A is a perspective view of yet another embodiment of the present invention.

In addition to the alternative embodiments described above, FIGS. 7 A-7D show yet another alternative embodiment of the present invention including inserter 410, which can be attached to and rotate an implant 36. The shaft 14 of inserter 410 is connected from the handle 12 to an attachment grip cage 418. At least two attachment grips 422 exit the distal end of the attachment grip base 418 and are configured to rotate towards each other and grab an implant (not shown). The attachment grips 422 are connected by an attachment grip pivot 424, which is contained in the attachment grip base 418. The attachment pivot 424 is also confined by a tensioning slot 425 in the attachment grip pivot tensioner 426. Rotation of the attachment actuator 24 in one direction tensions the attachment shaft 26 which retracts the attachment grip pivot tensioner 426. This action pulls the attachment grip pivot 424 further into the attachment grip cage 418 and up against the anchor pocket 428 preventing the attachment grip pivot 424 from translating in the tensioning slot 425. A slight rotation of the attachment actuator 24 in the other direction allows the attachment grip pivot 424 to move away from the anchor pocket 428, which in turn allows the attachment grip pivot 424 to translate in the tensioning slot 425. The translation of the attachment grip pivot 424 in the tensioning slot 425 results in the pivoting of the attachment grips 422 relative to the attachment grip cage. This enables implant 36 rotation. Further rotation of the attachment actuator 24 in the other direction moves attachment grip pivot 424 and the attachment grips 422 out of the front of the attachment grip cage 418 allowing the attachment grips 422 to separate and release the implant 36. In this manner the attachment actuator 24 can be used to control both implant attachment/release and implant rotation relative to the inserter 410.

Figure 8:
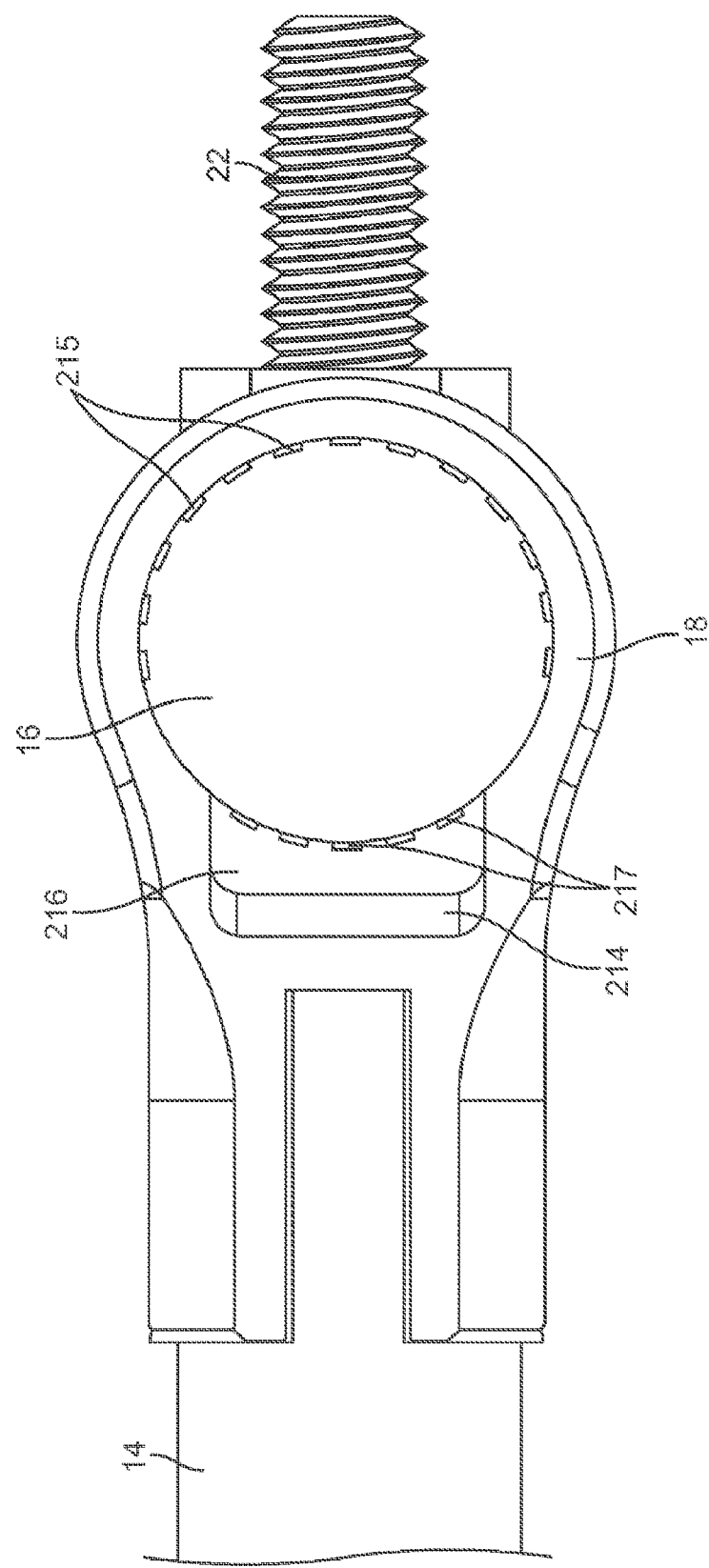
FIG. 8 is an enlarged side view of the attachment end of an insertion handle according to an embodiment of the present invention.

In previous embodiments the pivot lock 216 included engagement faces 217 configured to engage engagement faces 219 on the pivot head 16 and lock it rotationally. In an alternative embodiment, shown in FIG. 8, the engagement faces 217 on the pivot lock 216 are configured to create friction against the pivot head 16 to lock it rotationally. The engagement faces 217 are also configured to allow fluid to flow between the pivot lock 216 and the pivot head 16. One way to accomplish this is to provide squared off teeth on one of the opposed faces as shown. This is advantageous in that the engagement faces 217 provide for ease of cleaning of the inserter 10 between uses. Furthermore, engagement faces 215 can be provided on the pivot head to engage the pivot cage 218 and to create both friction and ease of cleaning between the pivot head 16 and the pivot cage 18.

Figure 9B:
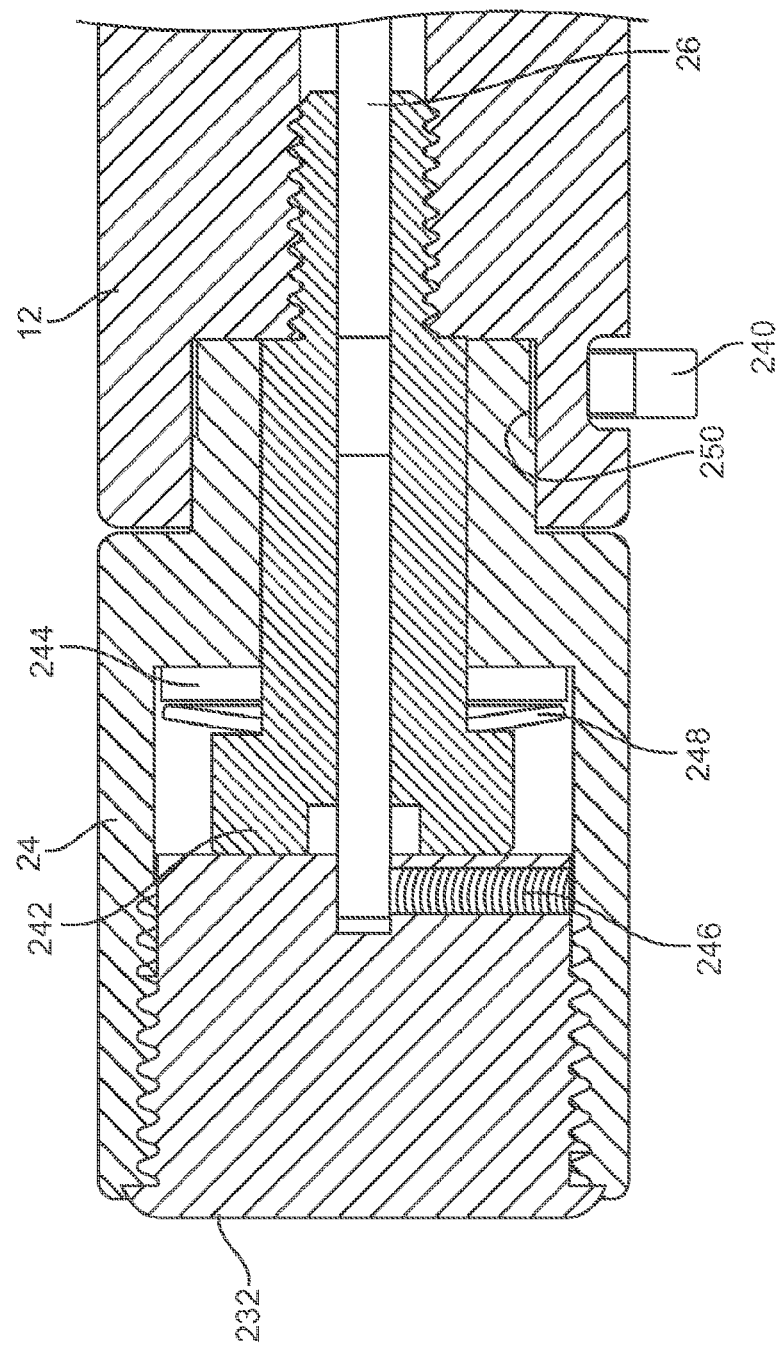
FIG. 9B is a side cross-sectional view of the embodiment shown in FIG. 9A.
Figure 9C:
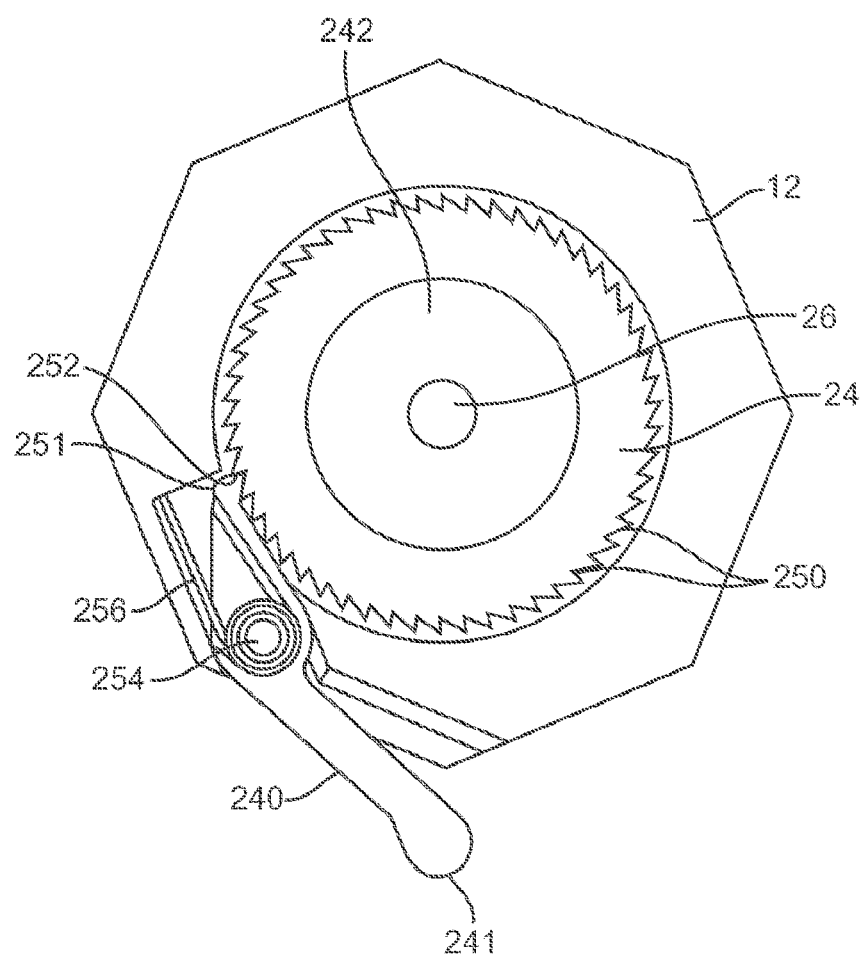
FIG. 9C is an axial cross-sectional view of the embodiment shown in FIG. 9A taken through line A-A.

Use of the inserter 10 to place an implant 36 into an intervertebral space 50 can include placing many loads and moments on the distal end of the inserter 10. Those loads and moments placed on the attachment actuator 24 can cause undesired rotation of the attachment actuator. Axial impact forces on the order of 55 lbs or more may be placed on the distal end of the inserter 10. Torques may be placed about any axis of rotation relative to the inserter shaft 14 ranging from 20 to over 100 inch pounds. Turning now to FIG. 9A-9C, another alternative embodiment of the current invention is depicted, which includes an actuator lock 240. The actuator lock 240 is mounted on the handle 12 by means of a pivot pin 254 (see FIG. 9C). The proximal end of the actuator lock 240 extends away from the handle 12 and the distal end 251 extends into the handle 12. The distal end 251 has a stop face 252, which is configured to engage a ratcheted surface 250 of the attachment actuator 24. An engagement spring 256 biases the stop face 252 against the ratcheted surface 250 and prevents the attachment actuator 24 from rotating in a direction that loosens the attachment shaft 26. Depressing the proximal end of the actuator lock 240 towards the handle 12 pivots the actuator lock 240 about the pivot pin 254 and disengages the stop face 252 from the ratcheted surface 250 allowing the attachment actuator to freely rotate. In the embodiment shown, the ratcheted surface 250 is biased relative to the stop face 252 to allow rotation of the attachment actuator 24 in the tightening direction even without depressing the proximal end of the actuator lock 240 towards the handle 12. Depressing of the actuator lock 240 is only needed to allow the attachment actuator 24 to loosen. It is apparent to those skilled in the art that the ratcheted surface 250 can also be configured to lock the attachment actuator 24 in both the loosening and the tightening directions unless the actuator lock 240 is depressed. Also shown in these figures is a cannulated connecting bolt 242, which connects the attachment actuator 24 to the handle 12. The inclusion of bearing 244 facilitates rotation in this connection. Axial force on the handle cap 232, which is often needed to direct the implant 36 into the intervertebral space 50 is accommodated by the beveled washer 248 located between the cannulated connecting bolt 242 and the bearing 244. Rotational force is transferred between the attachment actuator 24 and the attachment shaft 26 by the actuator connecting screw 246.

Figure 10:
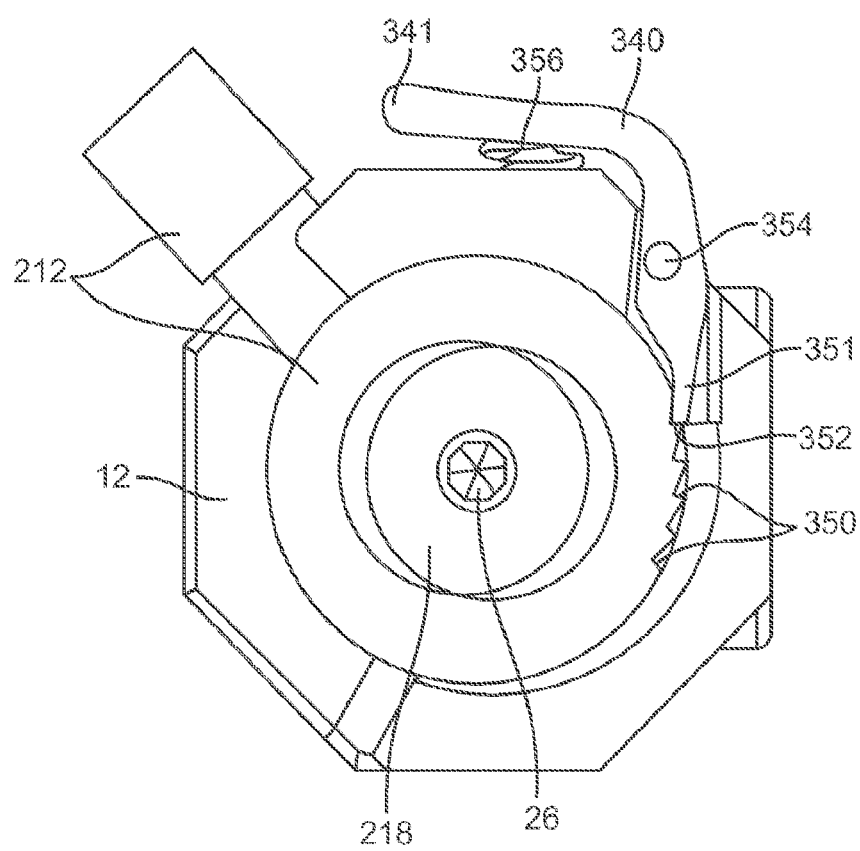
FIG. 10 is an axial cross-sectional view of yet another embodiment of the present invention.

In addition to the actuator lock 240 described above, embodiments of the present invention can also include a pivot lock 340 as shown in FIG. 10. The pivot lock 340 also has a proximal end 341 and a distal end 351 and pivots about a pivot lock pin 354. The distal end 351 has a pivot stop face 352 configured to engage a pivot ratcheted surface 350 located on a pivot lock actuator 212. A pivot lock spring 356 is positioned between the handle 12 and the proximal end 341 of the pivot lock 340 and biases the pivot stop face 352 into the pivot ratcheted surface 350 thereby preventing rotation of the pivot lock actuator 212. Depressing the proximal end 341 of the pivot lock 340 rotates the pivot lock 340 about the pivot lock pin 354 and disengages the pivot stop face 352 from the pivot ratcheting surface 350 allowing rotation of the pivot lock actuator 212. It will be apparent to those skilled in the art that insertion handles in accordance with embodiments of the present invention may include either or both of the pivot lock 340 and the actuator lock 240.

Figure 11A:
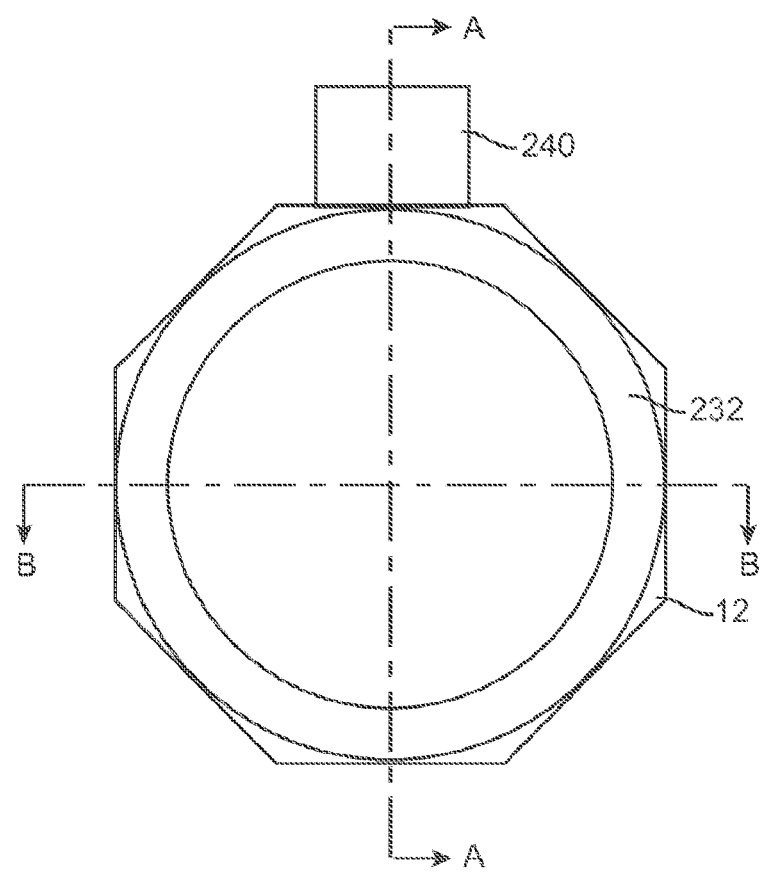
FIG. 11A is an end view of yet another embodiment of the present invention.
Figure 11B:
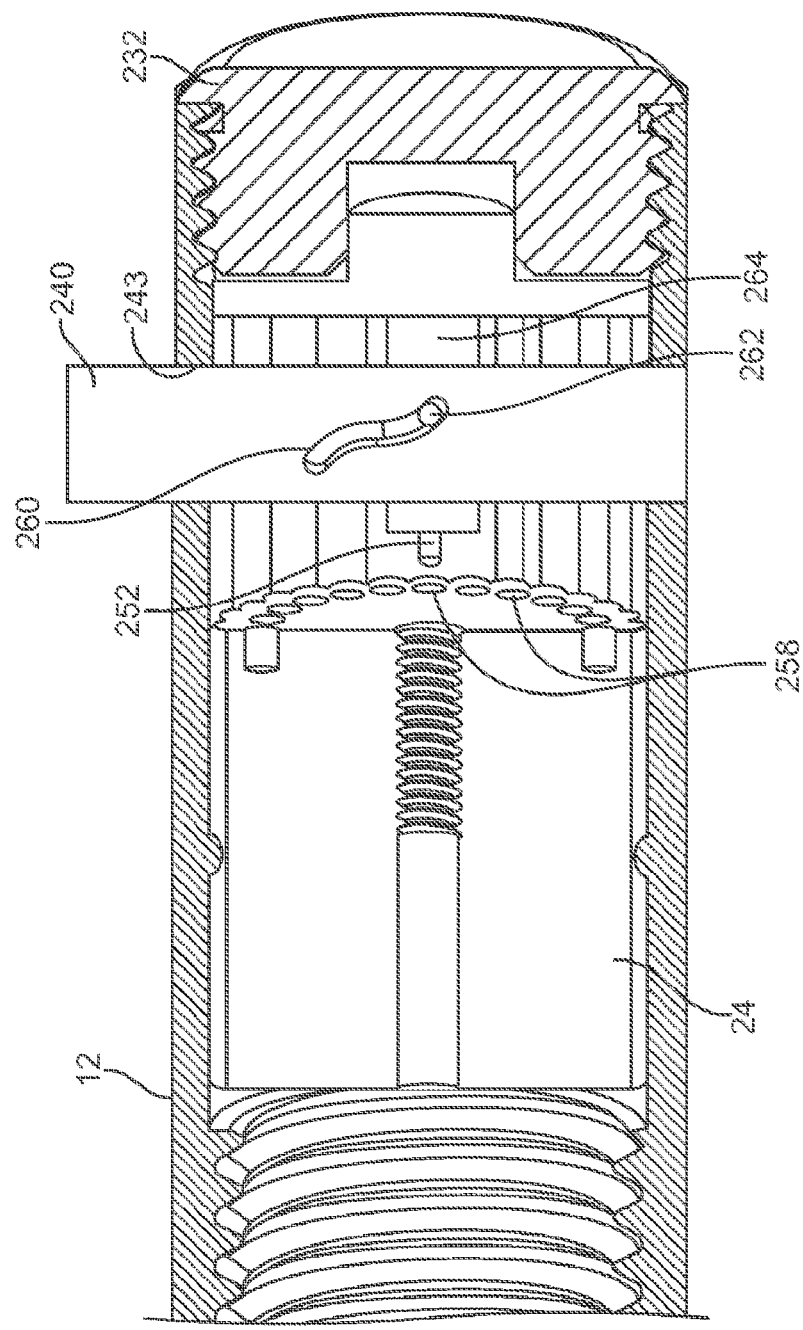
FIGS. 11B and 11C are side cross-sectional views of the embodiment shown in FIG. 11A taken through line A-A with the actuator lock in different positions.
Figure 11C:
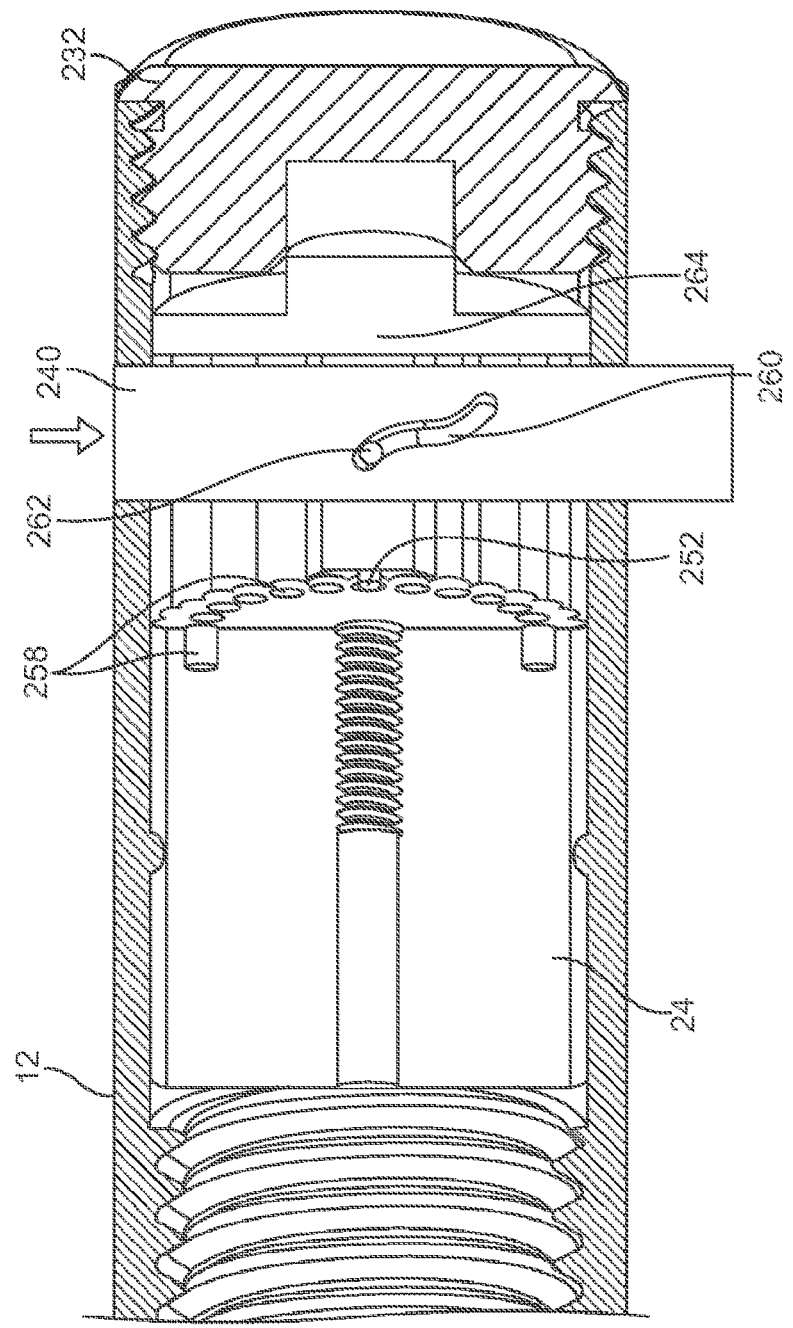
Figure 11D:
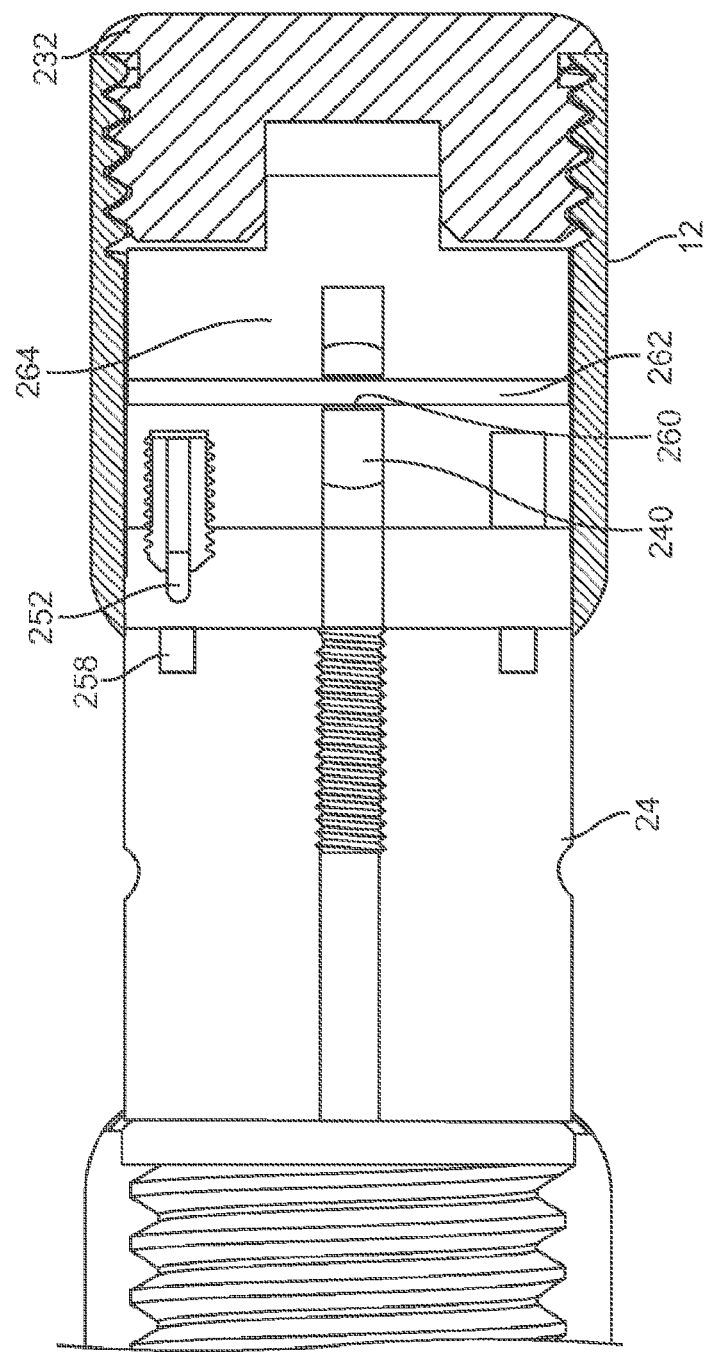
FIG. 11D is a side cross-sectional view of the embodiment shown in FIG. 11A taken through line B-B.

FIGS. 11A-D depict another alternative embodiment of the actuator lock 240, wherein the attachment shaft 26 is removed as shown in FIGS. 11B, C and D for clarity. In this embodiment the actuator lock 240 is mounted in through hole 243 that passes through the handle 12. The actuator lock 240 contains a cam slot 260, which is configured to engage a transfer pin 262 mounted on the locking carriage 264. The locking carriage 264 is contained in the handle 12 between the handle cap 232 and the attachment actuator 24. The locking carriage 264 contains the stop face 252, which is configured to be received by one of several stop holes 258 located on the attachment actuator 24. Depressing the actuator lock 240 (arrow in FIG. 11C) causes the cam slot 260 to force the transfer pin 262 distally. This action in turn translates the locking carriage 264 and the stop face 252 distally such that the stop face 252 engages one of the stop holes 258 and prevents rotation of the attachment actuator 24. Pressing the actuator lock 240 in the other direction will disengage the stop face 252 from the stop hole 258 and allow rotation of the attachment actuator 24. This alternative locking embodiment can be used for preventing movement of either the attachment actuator 24 or the pivot lock actuator 212. It will be apparent to those skilled in the art that any manner of actuator locks can be used to prevent movement of either or both of the attachment actuator 24 or the pivot locking actuator 212 without departing from the present invention.

Figure 12A:
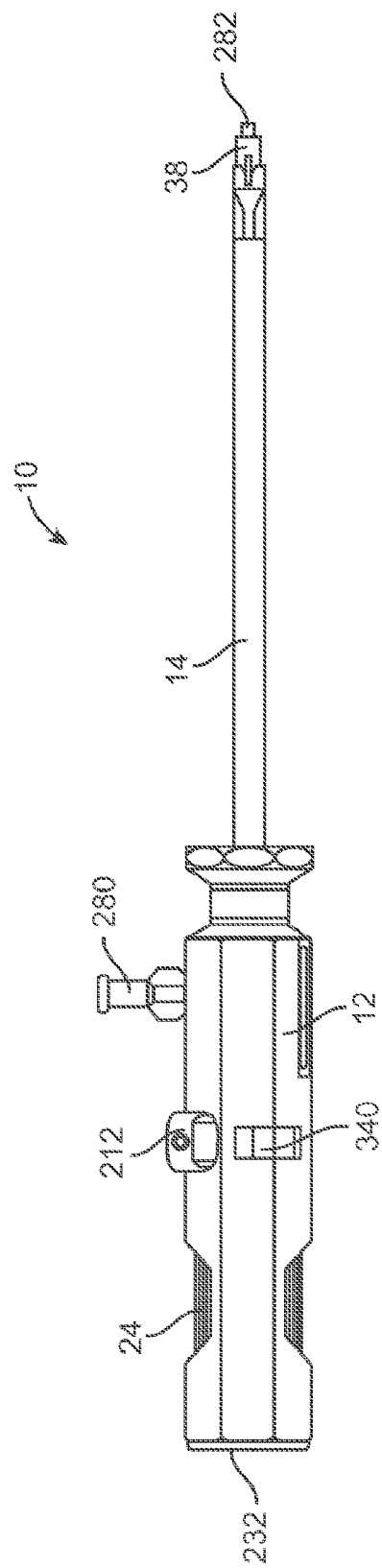
FIGS. 12A and 12B are side and top views respectively of yet another embodiment of the present invention.
Figure 12B:
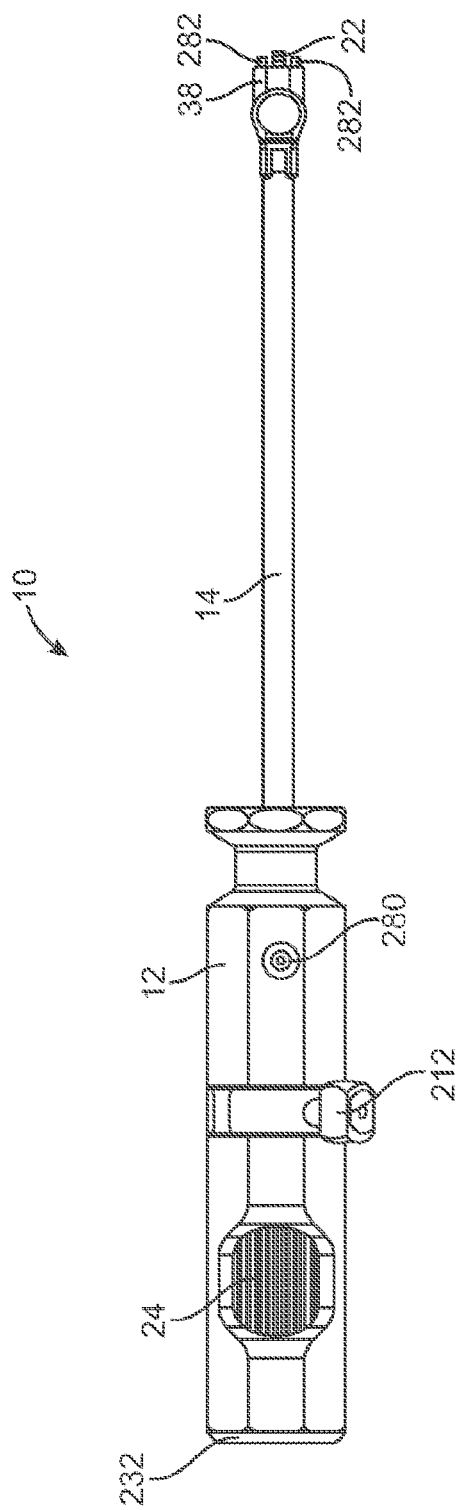
Figure 13A:
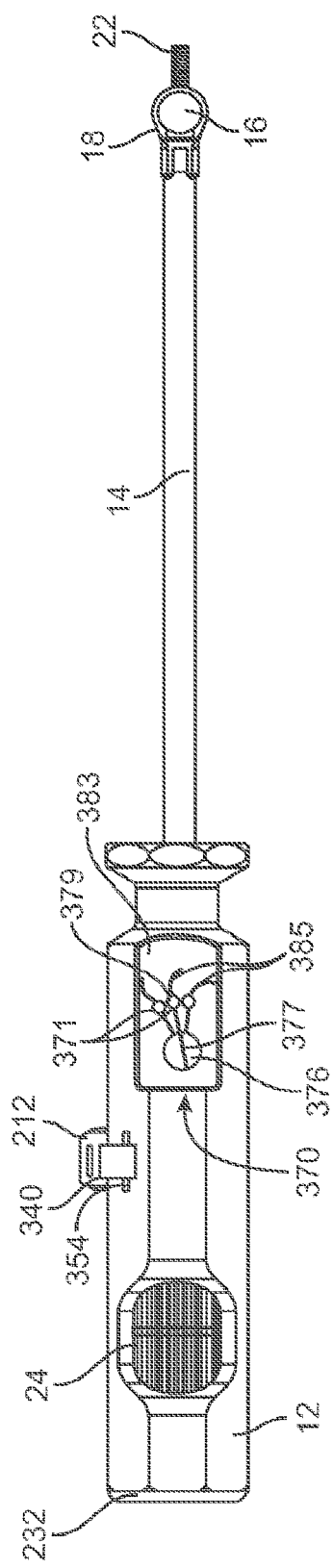
FIG. 13A is a top view of yet another embodiment of the present invention.
Figure 13B:
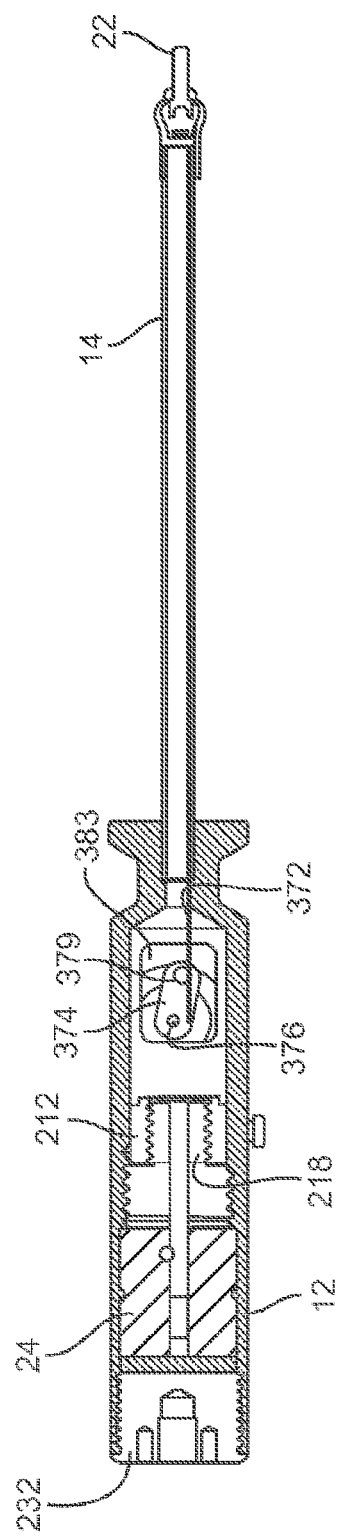
FIG. 13B is a cross-sectional view looking in the superior direction of the embodiment shown in FIG. 13A.
Figure 13C:
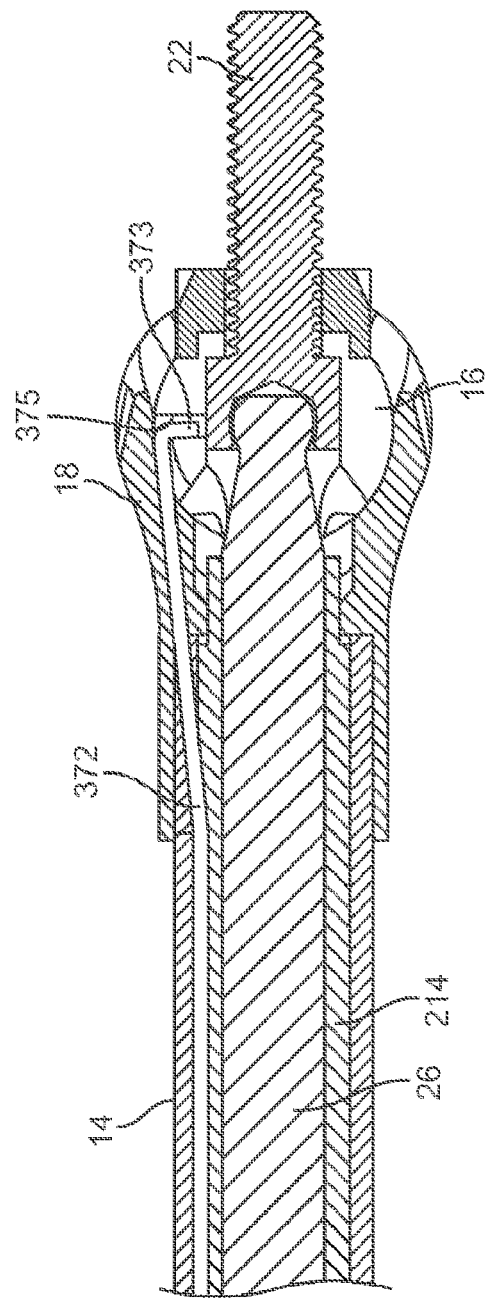
FIG. 13C is a detailed cross-sectional view of the distal end of the embodiment shown in FIG. 13B.
Figure 13D:
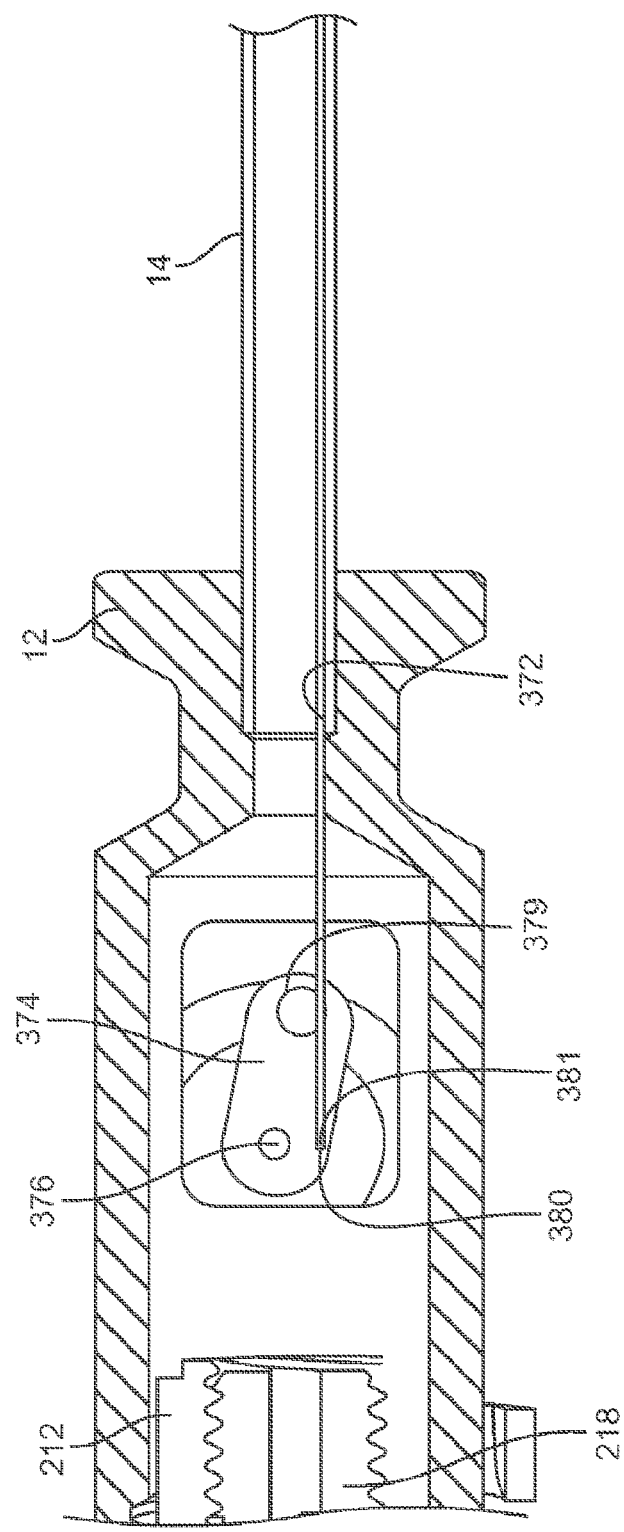
FIG. 13D is a detailed cross-sectional view of the proximal end of the embodiment shown in FIG. 13B.

FIGS. 12A and 12B depict another embodiment of the present invention that includes additional features. As was described above for the embodiment described in connection with FIG. 4, the inserter 10 can include access tubing 112. The access tubing 112 can interface with an implant 36 by means of implant connectors 282 located at the distal end of the inserter 10. Connectors 282 may extend through and from implant interface 38. The connectors can facilitate any manner of interaction with the implant including but not limited to electrical current, optical information, rotational power, fluid pressure, material transport. This interaction can flow one way or the other or both. The inserter 10 can also include an external connector 280 to further allow interaction through the inserter 10 with the implant 36 by means of the implant connectors 282. The external connector 280 can be configured for any manner of interaction between the inserter 10 and other equipment required for surgery including suction, aspiration, irrigation, injection, illumination, coagulation or other such equipment that is commonly used in surgery.

In one exemplary embodiment, the external connector 280 is configured to connect with a saline filled syringe which is used to supply pressurized saline to the implant 36 through the implant connectors 282 in order to expand the implant to a larger size after being implanted through a minimally invasive surgical opening. One example of such an expandable implant is shown and described in co-pending U.S. patent application Ser. No. 11/535,432 filed Sep. 26, 2006, entitled "Selectively Expanding Spine Cage, Hydraulically Controllable in Three Dimensions for Enhanced Spinal Infusion," which is incorporated by reference herein in its entirety. In another exemplary embodiment, the external connector 280 is configured to supply bone graft and or bone morphogentic protein to the implant to facilitate bony fusion. Although the embodiment shown in FIGS. 12A and B includes a single external connector 280 leading to two implant connectors 282, any number of either of these connectors are possible without departing from the scope of the current invention.

In addition to providing an interaction or exchange function between the implant 36 and the inserter 10 as described above, the implant connectors 282 also provide a torque transfer function. As the implant connectors 282 are spaced from the attachment screw 22, the implant connectors 282 provide resistance to any relative rotation between the implant 36 and the implant interface 38. This is particularly important as the attachment screw 22 engages the implant 36 through rotational movement. The one or more implant connectors 282 help to prevent any undesired rotation and subsequent loosening of the implant 36 relative to the inserter 10. For this purpose, implant connectors 282 should have sufficient strength to resist torque in a given application. Persons of ordinary skill in the art may design the size and shape of the implant connectors based on the teachings contained herein in order to withstand anticipated torque for any appropriate medical implant and its intended application. For example, implant connectors 282 can be fabricated from 304 stainless steel and extend 0.5 inches from the implant interface 38 at a location 0.25 inches from the central axis of the implant interface 38 such that they are rigid enough to resist the 100 inch pounds of rotation force placed on the implant 36. Utilization of the implant connectors for this purpose obviates the need for separate torque bearing structures such as keyways and the like, thus simplifying the engagement surfaces between the implant and inserter.

A detailed description has been given of the pivoting function in embodiments of the present invention and possible variations thereof. In many surgical procedures, due to the minimally invasive nature and/or due to the proximal anatomy, the physician may not be able to clearly see in which rotational position of the pivot head 16 is set. It therefore may be desirable in some embodiments to provide a position indicator 370 to indicate rotational position information as shown in FIGS. 13A-13D (attachment shaft 26 and pivot lock shaft 214 are removed for further clarity in FIGS. 13B and 13D). The position indicator 370 includes a position pivot 376, a position actuator 372, a position lever 374, a position cover 383, and a position marker 379. The distal end of the position actuator 372 has a bend 373 which is configured to be received by a distal pocket 375 in the pivot cage 16. The position actuator 372 extends from the pivot cage 16 back through the shaft 14 between the shaft 14 and the pivot lock shaft 214. Inside the handle 12, the position actuator 372 has a proximal bend 381, which is configured to be received by a proximal pocket 380 in the position lever 374. Rotation of the pivot cage 16 creates translation of the position actuator 372, which results in rotation of the position lever 374 about the position pivot 376. The rotating position lever 374 rotates the position marker 379, which can be viewed through different position openings 371 in the position cover 383. The position cover 383 can also have position icons 385, which may correspond to different rotational positions of the distal end of the inserter 10 to provide additional visual information that relates the position marker's 379 location in the position opening 371 to a distal end configuration. In addition the position pivot 376 can have a position pointer 377 on its exposed end which also rotates with the pivot 376 to provide additional visual rotation information. Alternatively, the position indicator may be used to position the angle of the pivot head 16 by user manipulation of a member extending outward from position lever 374.

Figure 14A:
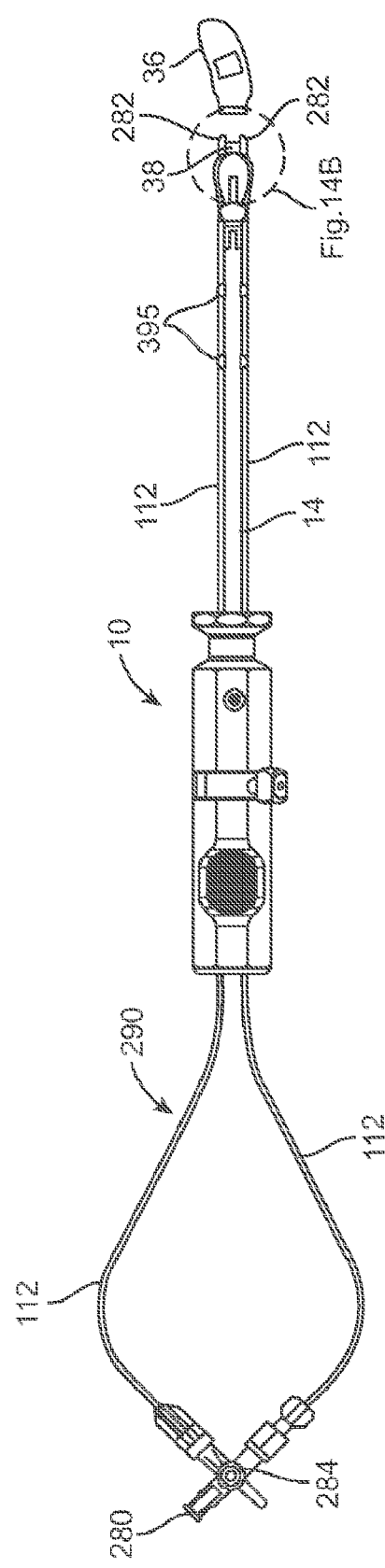
FIG. 14A is a top view of yet another embodiment of the present invention.

Although embodiments of the present invention described above include certain functions such as the exchange and interface functions with the implant, alternative embodiments of the present invention may provide those functions with a separate device. For example, turning to FIGS. 14A and 14B, an embodiment of an inserter 10 is shown that interfaces with a tubing set 290 both of which are configured to interface with an implant 36. The distal end of the tubing set 290 includes an implant interface 38 with implant connectors 282 to interface with the implant 36. The tubing set 290 also includes access tubing 112 and shaft clips 395, which are configured to constrain the access tubing 112 to the inserter shaft 14. The tubing set 290 further may include at least one external connector 280 at the proximal end, which is configured as described above to interface with other surgical equipment. In addition, the tubing set 290 may include a diverter valve 284. The diverter valve 284 is configured to open or close the connection between the external connector 280 and one or more access tubing 112. In the embodiment shown in FIG. 14A, the diverter valve 284 is configured to either provide openings to both access tubing 112 simultaneously, to close the opening to one or the other access tubing 112, or to close the openings to both access tubing 112 simultaneously. Providing a kit that contains the combination of the inserter 10 and various configurations of access tubing 290 enables more flexibility to the physician to use the current invention to insert and manipulate a wide variety of implants.

Figure 14B:
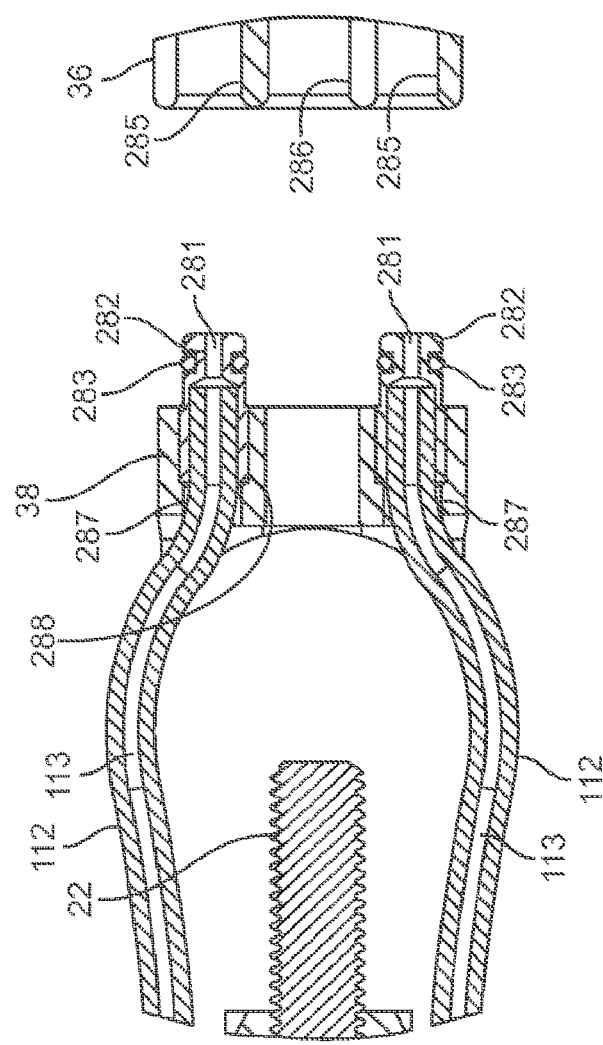
FIG. 14B is an enlarged section view of the embodiment in FIG. 14A at circle B.

As better seen in FIG. 14B, connectors 282 are formed as separate members inserted and secured in implant interface 38. Each connector 282 includes a passage 281 that communicates with tubing 112. Tubing 112 enters the back of interface 36 through openings 287 in which the connectors 282 are mounted. O-ring type seals 283 are provided to form a tight seal with corresponding passages 285 in implant 36. Central passageway 288 is provided for engagement screw 22 to freely pass through interface 38 for engagement with the implant. The mating face of implant 36 is also provided with a threaded hole 286 to receive attachment screw 22.

The present invention can be fabricated from numerous materials know to those skilled in the art. For example the handle 12, shaft 14, pivot cage 18 and pivot head 26 can all be made from any one of the number of biocompatible metals such as titanium, titanium alloy, or stainless steels including 303 and 304. The attachment actuator 24, external connector 280 implant interface 38 can all be made of a polymer such as polyacetal (e.g., Delrin®) or polyether ether keton (PEEK). The entire inserter 10 can be made of inexpensive materials so that it is single use and disposable or of more durable materials so that it can be cleaned and reused several or even hundreds of times.

Terms such as "element," "member," "device," "section," "portion," "step," "means" and words of similar import when used in the following claims shall not be construed as invoking the provisions of 35 U.S.C. § 112(6) unless the following claims expressly use the term "means" followed by a particular function without specific structure or expressly use the term "step" followed by a particular function without specific action. All patents and patent applications referred to above are hereby incorporated by reference in their entirety.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

The invention claimed is:

1. An instrument for inserting a medical implant, comprising:
   a handle;
   an outer shaft extending from the handle along a shaft axis;
   an inner shaft extending at least partially through the outer shaft;
   an actuator coupled to the handle and configured to cause movement of the inner shaft within the outer shaft; and
   an attachment screw for engagement with a medical implant, the attachment screw extending through an elongated window opening, and the attachment screw being pivotable about a pivot axis extending transverse to the shaft axis such that a longitudinal axis of the attachment screw is pivotable between a plurality of angles within the elongated window opening, wherein the attachment screw is coupled with the inner shaft to permit rotational drive of the attachment screw about its longitudinal axis while the attachment screw is positioned at any of the plurality of angles.

2. The instrument of claim 1, further comprising a locking mechanism operable to selectively fix the angle of the attachment screw.

3. The instrument of claim 1, wherein the attachment screw is coupled with the inner shaft via a universal joint.

4. The instrument of claim 1, further comprising a pivot head received within a cage, wherein the attachment screw is received within the pivot head, and wherein the pivot head is rotatable about the pivot axis to pivot the attachment screw between the plurality of angles.

5. The instrument of claim 4, further including an implant interface configured to engage the implant, wherein the attachment screw extends through the implant interface, and wherein the implant interface is integrally formed as a monolithic member with the pivot head.

6. The instrument of claim 4, further comprising a locking mechanism operable to selectively fix the angle of the attachment screw.

7. The instrument of claim 6, wherein the cage defines a wall that is deformable such that an inner surface of the wall compressively engages the pivot head to fix the angle of the attachment screw.

8. The instrument of claim 6, wherein the cage is adapted to constrict around the pivot head to fix the angle of the attachment screw.

9. The instrument of claim 6, wherein the locking mechanism includes a pivot lock that advances into engagement with the pivot head to fix the angle of the attachment screw.

10. The instrument of claim 9, wherein the handle includes a pivot lock actuator to control the advancement of the pivot lock.

11. The instrument of claim 9, wherein the pivot lock includes an engagement surface for engaging a corresponding surface of the pivot head, and wherein the engagement surface is shaped to conform to a shape of the corresponding surface of the pivot head.

12. The instrument of claim 11, wherein the engagement surface of the pivot lock includes a plurality of first facets arranged to engage a plurality of second facets on the corresponding surface of the pivot head.

13. The instrument of claim 11, wherein the engagement surface of the pivot lock includes a plurality of first teeth arranged to mesh with a plurality of second teeth on the corresponding surface of the pivot head.

14. The instrument of claim 11, wherein the engagement surface of the pivot lock includes a plurality of recesses.

15. The instrument of claim 11, wherein the corresponding surface of the pivot head includes a plurality of recesses.

16. The instrument of claim 1, further including an implant interface configured to engage the implant, wherein the attachment screw extends through the implant interface, and wherein the implant interface is pivotable along with the attachment screw about the pivot axis.

17. The instrument of claim 16, wherein the implant interface includes a connector extending therefrom and configured to engage the implant to prevent relative rotation between the implant and the implant interface.

18. The instrument of claim 16, wherein the implant interface includes a passage for receiving a tube for providing fluid communication with a port on the implant.

19. The instrument of claim 1, further including a tube for providing fluid communication with a port on the implant, the tube extending along and external to the outer shaft.

20. The instrument of claim 19, further including a shaft clip for coupling the tube to the outer shaft.

* * * * *